(12) United States Patent
Kiesel et al.

(10) Patent No.: US 7,291,824 B2
(45) Date of Patent: Nov. 6, 2007

(54) PHOTOSENSING THROUGHOUT ENERGY RANGE AND IN SUBRANGES

(75) Inventors: Peter Kiesel, Palo Alto, CA (US);
Oliver Schmidt, Palo Alto, CA (US);
Oliver Wolst, Nürtingen (DE)

(73) Assignee: Palo Alto Research Center Incorporated, Palo Alto, CA (US)

( * ) Notice: Subject to any disclaimer, the term of this patent is extended or adjusted under 35 U.S.C. 154(b) by 104 days.

(21) Appl. No.: 11/316,438

(22) Filed: Dec. 22, 2005

(65) Prior Publication Data
US 2007/0145236 A1 Jun. 28, 2007

(51) Int. Cl.
*G01J 3/50* (2006.01)
(52) U.S. Cl. ............... 250/208.2; 250/226; 250/578.1; 356/410; 356/411; 356/434; 356/435
(58) Field of Classification Search ........ 250/573–576, 250/578.1, 226, 208.1; 356/410, 411, 434, 356/435
See application file for complete search history.

(56) References Cited

U.S. PATENT DOCUMENTS

| | | | |
|---|---|---|---|
| 2,708,389 | A | 5/1955 | Kavanagh |
| 3,973,118 | A | 8/1976 | LaMontagne |
| 4,081,277 | A | 3/1978 | Brault et al. |
| 4,514,257 | A | * 4/1985 | Karlsson et al. ............. 162/49 |
| 4,573,796 | A | * 3/1986 | Martin et al. ............... 356/318 |
| 4,764,670 | A | 8/1988 | Pace et al. |
| 4,957,371 | A | 9/1990 | Pellicori et al. |
| 4,976,542 | A | 12/1990 | Smith |
| 5,144,498 | A | 9/1992 | Vincent |
| 5,166,755 | A | 11/1992 | Gat |
| 5,305,082 | A | 4/1994 | Bret |

(Continued)

FOREIGN PATENT DOCUMENTS

WO        WO 95/20144        7/1995

(Continued)

OTHER PUBLICATIONS

"Developing technology: HPLC-Chip/MS", Agilent Technologies, printed from www.chem.agilent.com on Aug. 2, 2005, 2 pages.

(Continued)

*Primary Examiner*—Georgia Epps
*Assistant Examiner*—Stephen Yam
(74) *Attorney, Agent, or Firm*—Leading-Edge Law Group, PLC; James T. Beran

(57) ABSTRACT

An integrated circuit (IC) includes a photosensor array, some cells of which are reference cells that photosense throughout an application's energy range, while other cells of which are subrange cells that photosense within respective subranges. For example, the subrange cells can receive photons in their respective subranges from a transmission structure that has laterally varying properties, such as due to varying optical thickness. The reference cells may be uncoated or may also receive photons through a transmission structure such as a gray filter. Subrange cells and reference cells may be paired in adjacent lines across the array, such as rows. Where photon emanation can vary along a path, quantities of incident photons photosensed by subrange cells along the path can be adjusted based on quantities photosensed by their paired reference cells, such as with normalization.

30 Claims, 13 Drawing Sheets

U.S. PATENT DOCUMENTS

| | | | |
|---|---|---|---|
| 5,370,842 A * | 12/1994 | Miyazaki et al. | 422/82.06 |
| 5,572,328 A | 11/1996 | Fouckhardt et al. | |
| 5,682,038 A * | 10/1997 | Hoffman | 250/458.1 |
| 5,777,329 A | 7/1998 | Westphal et al. | |
| 5,784,507 A | 7/1998 | Holm-Kennedy et al. | |
| 5,792,663 A | 8/1998 | Fry et al. | |
| 5,801,831 A | 9/1998 | Sargoytchev | |
| 5,864,641 A | 1/1999 | Murphy et al. | |
| 5,876,674 A * | 3/1999 | Dosoretz et al. | 422/91 |
| 5,880,474 A * | 3/1999 | Norton et al. | 250/458.1 |
| 6,108,463 A | 8/2000 | Herron et al. | |
| 6,137,117 A | 10/2000 | Feldstein et al. | |
| 6,192,168 B1 | 2/2001 | Feldstein et al. | |
| 6,249,346 B1 | 6/2001 | Chen et al. | |
| 6,275,628 B1 | 8/2001 | Jones et al. | |
| 6,295,130 B1 | 9/2001 | Sun et al. | |
| 6,353,475 B1 | 3/2002 | Jensen et al. | |
| 6,399,405 B1 | 6/2002 | Chen et al. | |
| 6,405,073 B1 | 6/2002 | Crowley et al. | |
| 6,459,080 B1 | 10/2002 | Yin et al. | |
| 6,483,959 B1 | 11/2002 | Singh et al. | |
| 6,490,034 B1 | 12/2002 | Woias et al. | |
| 6,505,775 B1 | 1/2003 | Gu et al. | |
| 6,519,037 B2 | 2/2003 | Jung et al. | |
| 6,525,308 B1 | 2/2003 | Schmidt-Hattenberger | |
| 6,577,780 B2 | 6/2003 | Lockhart | |
| 6,580,507 B2 | 6/2003 | Fry et al. | |
| 6,603,548 B2 | 8/2003 | Church et al. | |
| 6,608,679 B1 | 8/2003 | Chen et al. | |
| 6,630,999 B2 | 10/2003 | Shroder | |
| 6,785,002 B2 | 8/2004 | Zarrabian et al. | |
| 6,800,849 B2 | 10/2004 | Staats | |
| 6,870,149 B2 | 3/2005 | Berezin | |
| 6,887,713 B2 | 5/2005 | Nelson et al. | |
| 2003/0000835 A1 | 1/2003 | Witt et al. | |
| 2003/0077660 A1 | 4/2003 | Pien et al. | |
| 2003/0235924 A1 | 12/2003 | Adams et al. | |
| 2004/0031684 A1 | 2/2004 | Witt | |
| 2004/0032584 A1 | 2/2004 | Honda et al. | |
| 2004/0132214 A1 | 7/2004 | Lin et al. | |
| 2004/0141884 A1 | 7/2004 | Unno et al. | |
| 2004/0145738 A1 | 7/2004 | Sun et al. | |
| 2004/0175734 A1 | 9/2004 | Stahler et al. | |
| 2004/0223881 A1 | 11/2004 | Cunningham et al. | |
| 2005/0042615 A1 | 2/2005 | Smith et al. | |
| 2005/0068526 A1 | 3/2005 | Avrutsky | |
| 2005/0084203 A1 | 4/2005 | Kane | |
| 2006/0039009 A1 | 2/2006 | Kiesel et al. | |
| 2006/0046312 A1 | 3/2006 | Kiesel et al. | |
| 2006/0092413 A1 | 5/2006 | Kiesel et al. | |
| 2006/0121555 A1 | 6/2006 | Lean et al. | |

FOREIGN PATENT DOCUMENTS

| | | |
|---|---|---|
| WO | WO 00/62050 | 10/2000 |

OTHER PUBLICATIONS

Singh, K., and Goddard, N.J., "Leaky ARROW Waveguides for Optical Chemical and Biosensors". (Abstract Submitted to Biosensors 1998), printed from dias.umist.ac.uk on Aug. 1, 2005, 2 pages.

"Abstracts of Published Work", printed from dias.umist.ac.uk on Aug. 1, 2005, 3 pages.

Goddard, N.J., Singh, K., Bounaira, F., Holmes, R.J., Baldock, S.J., Pickering, L.W., Fielden, P.R., and Snook, R.D., "Anti-Resonant Reflecting Optical Waveguides (ARROW), as Optimal Optical Detectors for MicroTAS Applications", printed from dias.umist.ac.uk on Aug. 1, 2005, pp. 1-5.

Sivaprakasam, V., Huston, A., Eversole, J., and Scotto, C., Multiple UV Wavelength Excitation and Fluorescence of Bioaerosols, 2nd Joint Conference on Point Detection, Williamsburg, VA, 2004, 10 pages.

Koch, M., Evans, A.G.R., and Brunnschweiler, A., "Design and fabrication of a micromachined Coulter counter", J. Micromech. Microeng. 9, 1999, pp. 159-161.

Agilant Technologies, "Agilent 83453B High-Resolution Spectrometer—Technical Specifications", Feb. 2005, pp. 1-8.

Liu, G.L., and Lee, L.P., "Nanowell surface enhanced Raman scattering arrays fabricated by soft-lithography for label-free biomolecular detections in integrated microfluidics", Applied Physics Letters, vol. 87, 2005, pp. 1-3.

Devasenathipathy, S., and Santiago, J.G., "3 Electrokinetic Flow Diagnostics" in Breuer, K.S., Ed., Micro-and Nano-Scale Diagnostic Techniques, Springer Verlag, New York, 2003, pp. 121-166.

Becker, H., and Gartner, C., "Polymer microfabrication methods for microfluidic analytical applications", Electrophoresis, vol. 21, 2000, pp. 12-26.

Singh, K., Liu, C., Capjack, C., Rosmus, W., and Backhouse, C.J., "Analysis of cellular structure by light scattering measurements in a new cytometer design based on a liquid-core waveguide", IEEE Proc.-Nanobiotechnol., vol. 151, No. 1, Feb. 2004, pp. 10-16.

Adams, M.L., Enzelberger, M., Quake, S., and Scherer, A., "Microfluidic Integration on detector arrays for absorption and fluorescence micro-spectrometers,"Sensors and Actuators A, vol. 104, 2003, pp. 25-31.

* cited by examiner

FIG. 2
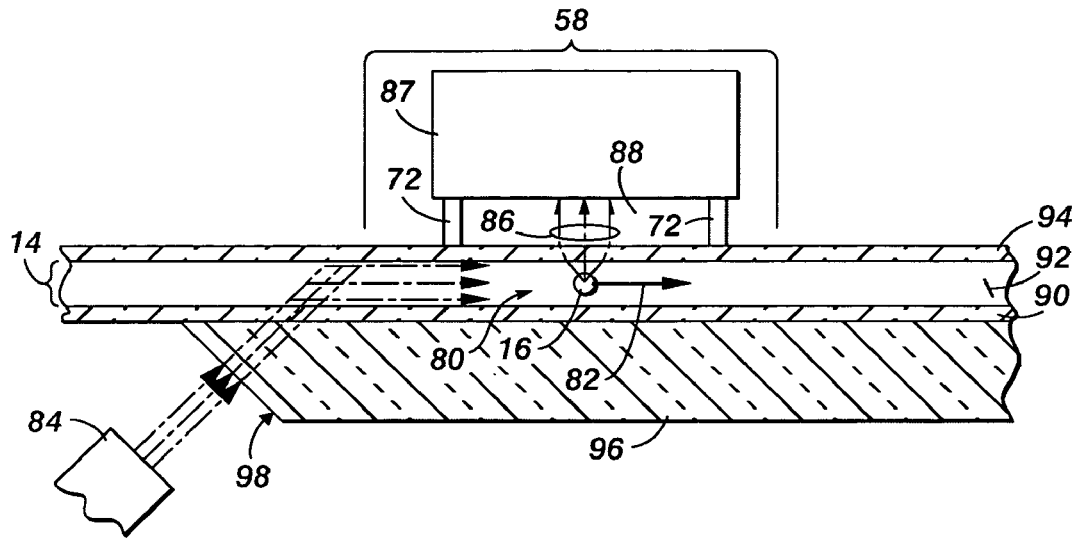
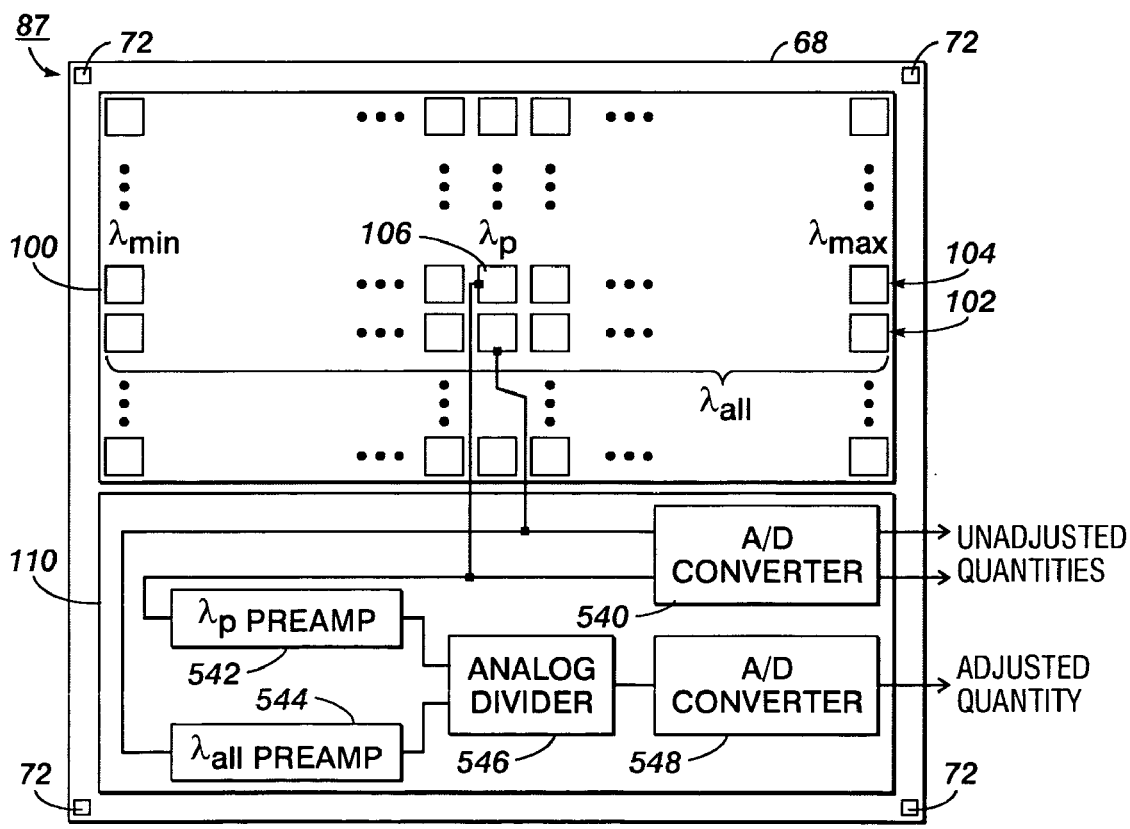
FIG. 3

FIG. 12
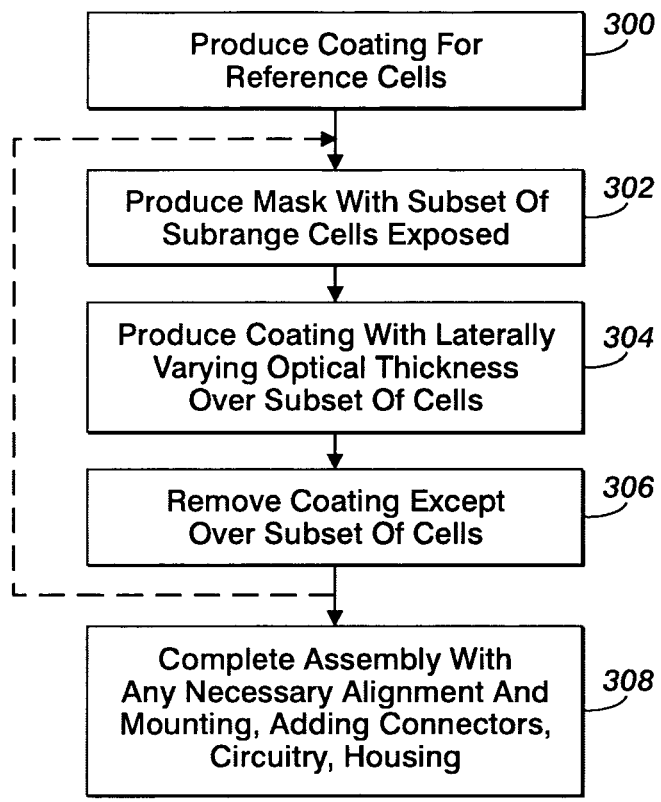
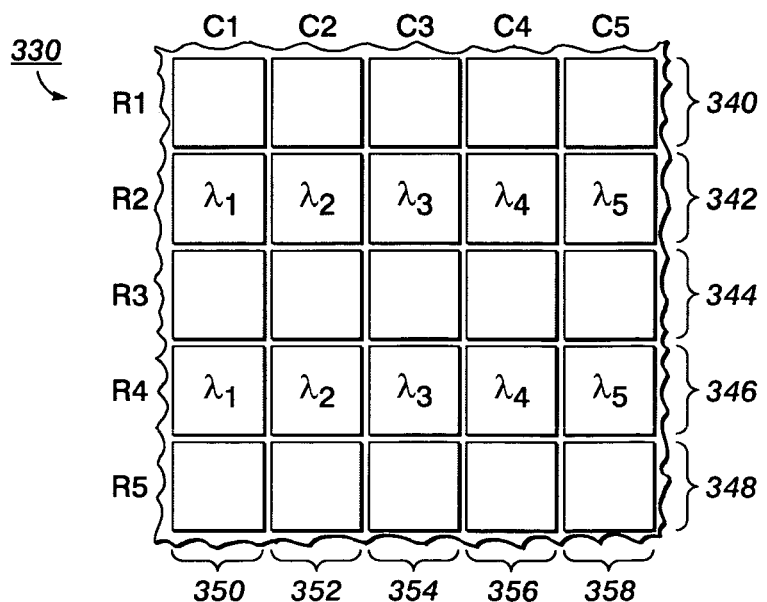
FIG. 13

PHOTOSENSING THROUGHOUT ENERGY RANGE AND IN SUBRANGES

The present application is related to the following co-pending applications, each of which is hereby incorporated by reference in its entirety: "Chip-Size Wavelength Detector", U.S. patent application Ser. No. 10/922,870; "Biosensor Using Microdisk Laser", U.S. patent application Ser. No. 10/930,758; "Anti-resonant Waveguide Sensors", U.S. patent application Ser. No. 10/976,434; "Bio-Enrichment Device to Enhance Sample Collection and Detection", U.S. patent application Ser. No. 11/007,121; "Sensing Photon Energies of Optical Signals", U.S. patent application Ser. No. 11/315,926; "Sensing Photon Energies Emanating From Channels or Moving Objects", U.S. patent application Ser. No. 11/315,992; "Providing Light To Channels Or Portions", U.S. patent application Ser. No. 11/316,660; "Sensing Photon Energies Emanating from Channels", U.S. patent application Ser. No. 11/315,386; "Transmitting Light With Photon Energy Information", U.S. patent application Ser. No. 11/316,241; "Obtaining Analyte Information", U.S. patent application Ser. No. 11/316,303; and "Propagating Light to be Sensed", U.S. patent application Ser. No. 11/315,387.

BACKGROUND OF THE INVENTION

The present invention relates generally to photosensing, and more particularly to photosensing with photosensor arrays on integrated circuits (ICs).

U.S. Pat. No. 6,580,507 describes a system in which an array detector is positioned to monitor radiation from flow cell channels. A single detector chip is used to monitor sample and reference beams. Absorption or fluorescence can be monitored. Signals from pixels that detect different beams are summed to provide separate sample and reference powers, and a ratio can be obtained.

U.S. Pat. No. 5,166,755 describes a spectrometer apparatus in which a spectrum resolving sensor contains an opto-electronic monolithic array of photosensitive elements and a continuous variable optical filter. The filter can include a variable thickness coating formed into a wedge shape on a substrate or directly on the surface of the array. If polychromatic light, such as light reflected from a sample or a strip of a scene viewed from a spacecraft, passes through the variable filter and is spectrally resolved before incidence on the array, the output of all the elements in the array provides the spectral contents of the polychromatic light. High spectral resolving power is obtained by subtracting the output signals of adjacent elements in the array.

It would be advantageous to have improved techniques for photosensing with ICs.

SUMMARY OF THE INVENTION

The invention provides various exemplary embodiments, including methods, systems, and sensors. In general, the embodiments are implemented with integrated circuits that include photosensor arrays.

These and other features and advantages of exemplary embodiments of the invention are described below with reference to the accompanying drawings.

BRIEF DESCRIPTION OF THE DRAWINGS

FIG. 2 is a schematic cross-sectional view of the analyzer in FIG. 1, taken along the line 2-2.

FIG. 3 is a schematic plan view of an implementation of an assembly that can be used in FIG. 2, including an integrated circuit (IC) with a photosensor array.

FIG. 12 is a flow chart showing general operations that can be performed in producing a transmission structure, such as in FIGS. 4, 6, 8, or 9.

FIG. 13 is a schematic plan view of a segment of a photosensor array that could be used in an assembly as in FIG. 2.

DETAILED DESCRIPTION

Figure 1:
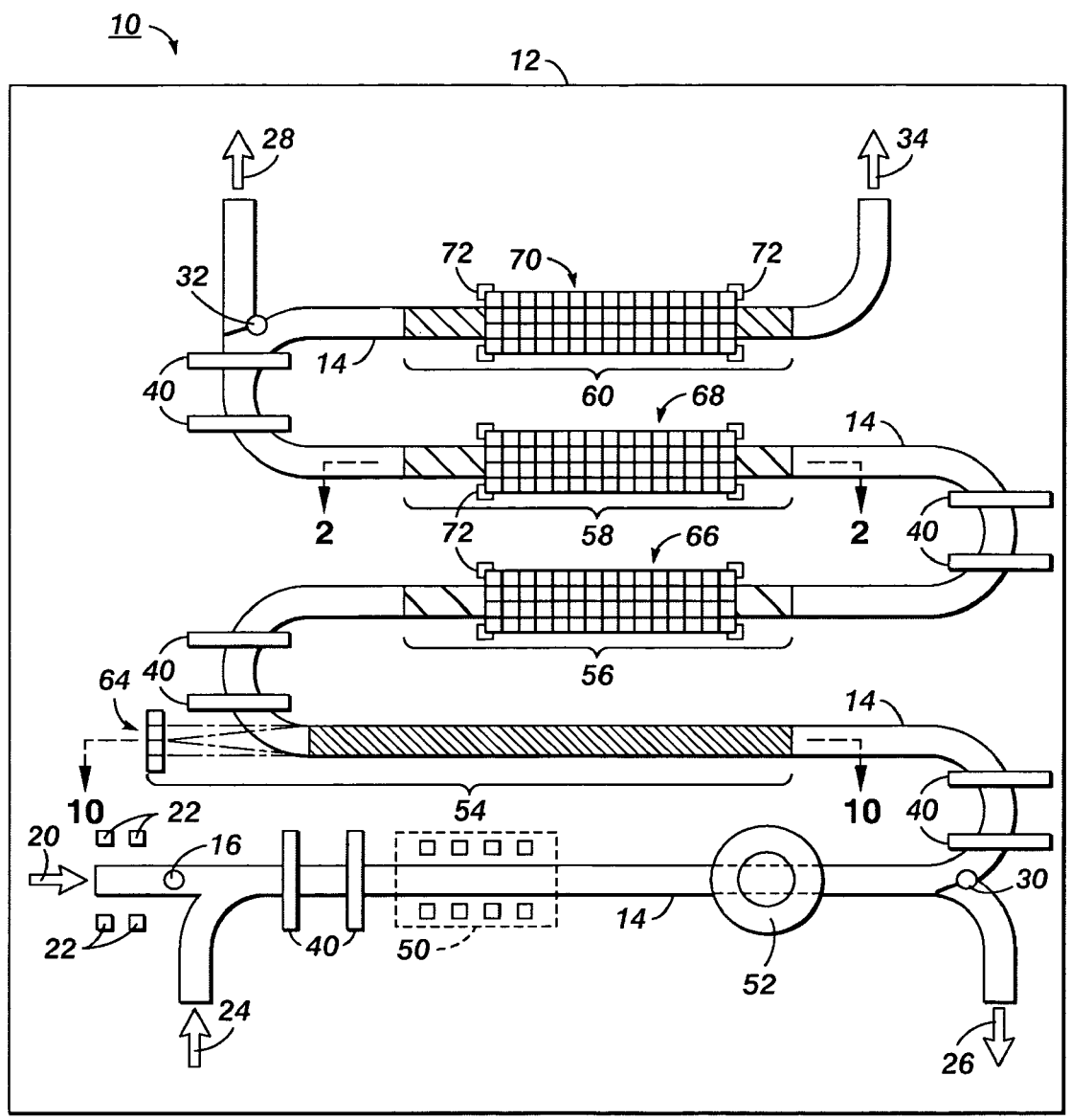
FIG. 1 is a schematic diagram of an analyzer on a fluidic structure.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon.

The various exemplary implementations described below address problems that arise in photosensing with arrays of cells. One such problem is that cells in an array may produce sensing results that include error solely due to inhomogeneities of various kinds.

The term "sensing" is used herein in the most generic sense of obtaining information from a physical stimulus; sensing therefore includes actions such as detecting, measuring, and so forth. A "sensor" is a component that performs some type of sensing, obtaining information from a physical stimulus. To "photosense" is to sense photons, and to "photosense quantity" of photons is to obtain information indicating a quantity of the photons. Photons that are photosensed are sometimes referred to herein as "incident photons".

A "photosensor" is used herein to refer generally to any element or combination of elements that senses photons, whether by photosensing quantity or any other information about the photons. A photosensor could, for example, provide an electrical signal or other signal that indicates sensed information, such as a signal indicating quantity of incident photons. If electrical sensing events occur in a photosensor in response to incident photons, the photosensor may integrate or otherwise accumulate the results of the electrical sensing events during a time period referred to herein as a "sensing period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, each application of photosensing has a characteristic energy range, referred to as the "application's energy range", which is the range of photon energies over which it is necessary to obtain information in order that the application satisfies the relevant performance criteria. For example, if an application uses helium arc lamps, its energy range could encompass helium's major emission peaks.

In general, the upper and lower boundaries and widths of ranges and subranges are approximate. To photosense quantity of photons "throughout", "within", or "in" a range or subrange means to obtain information about quantity of photons that are predominantly within the range or subrange. In typical cases, between 60-90% of the sensed quantity of photons having energies within the range or subrange, but the percentage could be lower or higher. In some applications, 90% or even 95% or more of the sensed quantity of photons have energies within the range or subrange. Where an application requires that a minimum percentage or other proportion of sensed quantity of photons have energies within a range or subrange, the minimum percentage or other proportion is referred to herein as the "application's minimum photon proportion".

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations described herein include features characterized as "cells" and "arrays", terms that are used with related meanings: An "array" is an arrangement of "cells". An array on an IC or other support structure may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

A "photosensor array" is an array in which some or all of the cells are or include photosensors. Accordingly, an IC "includes" a photosensor array if the IC includes an array of cells, and at least some of the cells include respective photosensors. A cell that includes a photosensor may also include "cell circuitry", such as circuitry that makes connections with the photosensor, that transfers signals to or from the photosensor, or that performs any other function other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry.

FIG. 1 shows schematically some components of analyzer 10 on support structure 12, a fluidic structure. Defined in support structure 12 is serpentine channel 14 through which an object 16 can travel, carried by a fluid or other appropriate substance. Object 16 can, for example, be a droplet or small volume of fluid that includes an analyte to be analyzed.

Object 16 enters channel 14 carried by a primary fluid illustrated by arrow 20, and can enter from a supply reservoir (not shown) and a sample well (not shown), with its entry into the primary fluid controlled by metering electrodes 22. The supply reservoir could, for example, be a microfabricated bio-enrichment device with a cell on which concentration occurs, as described in co-pending U.S. patent application Ser. No. 11/007,121, entitled "Bio-Enrichment Device to Enhance Sample Collection and Detection", and incorporated herein by reference in its entirety. Separated bands in the bio-enrichment sample well could be selectively directed into channel 14. Rather than electrical metering, as with electrodes 22, pressure metering could be used.

Although FIG. 1 illustratively shows an implementation with only one channel 14 receiving analyte samples from a single sample well (not shown) or other analyte container, analyte 10 could be implemented with any appropriate number of channels similar to channel 14, and with each channel receiving analyte samples from a respective sample well. Furthermore, each of the channels could have a different combination of components suitable to a specific type of analysis such as fluorescence spectroscopy, laser-induced fluorescence spectroscopy (LIF), absorption spectroscopy, excitation spectroscopy, Raman scattering, surface-enhanced Raman scattering (SERS), far-infrared spectroscopy, etc. Each sample well could continuously collect a specific analyte for stationary or post-detection schemes. The channels could be formed by subdividing a broad channel into several parallel channels.

Additional fluid to carry object 16 may enter as shown by arrow 24, such as to permit a constant flow rate or consistent flow independent of the analyte supply. The path followed by the fluid in channel 14 can be controlled through a number of devices. For example, the fluid, together with object 16 if appropriately positioned, can be purged at two outlets as illustrated by arrows 26 and 28 through toggling of valves 30 and 32, respectively, each of which is at a bifurcation junction. Rather than valves, other types of gates could be used, such as electric fields to selectively deflect objects; charged particles could be deflected by Coulomb force, and polarizable particles could be deflected by dielectrophoretic force. If the fluid is not purged by operating valves 30 and 32 or other similar valves (not shown) or by some other type of gate, it is purged at a final outlet from channel 14, illustrated by arrow 34.

The flow of the fluid can be maintained by conventional propulsion components such as electro-osmotic pumps 40 or some suitable hydraulic pressure pump appropriately positioned along the length of channel 14. A wide variety of other propulsion components could be used, including, for example, gas pressure pumps, positive displacement pumps, micro-peristaltic pumps, electro-kinetic pumps, piezo pumps, and thermal mode pumps. Various techniques for fluid propulsion are described in Devasenathipathy, S., and Santiago, J. G., "Electrokinetic Flow Diagnostics", in Breuer, K. S., Ed., *Micro and Nano-Scale Diagnostic Techniques*, Springer-Verlag, New York, 2003, pp. 113-154, incorporated herein by reference. In addition to maintaining flow of fluid, propulsion components can also perform system flush and initial fluid loading functions, with pressure driven techniques. Appropriate circuitry (not shown) can coordinate the various pumps and other components to work in a synchronized manner.

Pressure driven flow creates a parabolic velocity profile due to fluid resistance at the walls of a channel, which leads to band spreading. Spreading and other forms of band distortion will also be evident in fluid passing through one of the serpentine curves in channel 14. Appropriate techniques can be used to track discrete analytes and provide flow cross-section commensurate with analyte size.

Electro-osmotic flow (EOF) results from motion of ions inside the Debye layer due to an applied electric field in a channel direction. A Debye layer forms if the channel walls charge up when in contact with the solvent, e.g. water. The charged wall surface attracts oppositely charged counter ions, which concentrate in a thin layer next to the surface. The Debye layer has a thickness of $$\lambda_D = \left(\frac{\varepsilon kT}{q^2 n}\right)^{1/2},$$

where $\varepsilon$ indicates the dielectric constant, k indicates the Boltzman constant, T indicates the temperature, q indicates the ion charge, and n indicates the concentration of ions. Application of a potential difference in the direction of the channel causes the Debye layer to move with the electric field and, due to viscous drag, to create bulk fluid flow. The velocity profile is flat so that band distortion is a minimum. It should be noted, however, that EOF is dependent on wall charge, which is in turn affected by pH.

Various techniques can be used to control the flow of analytes, such as by directing them into different channels depending on their properties. This allows purging of benign or uninteresting particles, or the use of different detection schemes for different classes of particles that have been identified in initial detection steps. For example, the propulsion components can be coordinated with appropriate additional components for gating, metering, sorting, bifurcating, and otherwise logically controlling flow, such as with valves 30 and 32 and other appropriate devices controlled by switching electrodes and charge control.

Along channel 14 is a series of sensing components, each of which obtains information about object 16 as it travels within a respective straight portion of channel 14; the straight portions are separated by 180-degree curved portions, allowing a compact arrangement of several sensing components and interactive detection. Coulter counter 50 and Mie scatter sensor 52, for example, are conventional sensing components, illustratively along parts of one straight portion of channel 14. Coulter counter 50 is an example of an electrically based particle size detector, and could be implemented as described, for example, in Koch, M., Evans, A. G. R., and Brunnschweiler, A., "Design and Fabrication of a Micromachined Coulter Counter", *J. Micromech. Microeng.*, Vol. 9, 1999, pp. 159-161, incorporated herein by reference. Mie scatter sensor 52 is an example of an optical detector that relies on particle-induced scattering of light entering from the side of channel 14.

Coulter counter 50 can be implemented to size particles in the 1-10 µm range within a continuous liquid stream. The Coulter counter technique should also work for other particle sizes as long as the inner diameter of channel 14 in the sensing region is not more than an order of magnitude larger than the particles being measured. Also, larger particles are harder to handle in microfluidic systems, i.e. fluidic systems in which channels have maximum transverse inner dimensions less than 0.1 mm; in such systems, larger particles tend to sediment if their density is greater than that of the solvent.

In Coulter counter 50, particles suspended in an electrically conducting solution can be drawn through a small aperture between two electrodes. A voltage applied across the aperture creates a sensing zone, and each particle passing through the sensing zone displaces its own volume of conducting liquid. The particle has infinite resistance, even if itself conductive, because polarization effects at the particle-electrolyte interface prevent any current from flowing through the particle itself. Therefore, the particle's resistance causes a momentary increase of impedance across the aperture. This change in impedance produces a tiny current flow that can be received by an amplifier and converted into a voltage pulse large enough for accurate measurement.

The Coulter principle states that the amplitude of this pulse is directly proportional to the volume of the particle, so that scaling pulse heights in volume units provides information about particle size. A size distribution can be obtained and displayed.

Mie scattering is another conventional technique for determining particle size in a free stream. Mie scattering refers to the elastic interaction of electromagnetic waves with particles having diameter at least one-tenth of the wavelength of incident light. The radiation pattern is predominantly forward scatter, with an invariant scattered angular pattern that is symmetrical along the axis of incident light for a perfect sphere. The scattered intensity increases with sphere radius, so that large particles may be distinguished from small particles by the strength of light reflected from their surfaces at a given angle. Mie scattering using light of different wavelengths has been successfully applied to size measurements of single bioaerosol particles.

The series of sensing components also includes optical (e.g. visible or infrared) absorption sensing component 54, first fluorescence sensing component 56, second fluorescence sensing component 58, and Raman scatter sensing component 60. These are merely exemplary, however, and analyzer 10 could include any other suitable combination of sensing components, including some that are not connected in series. In particular, additional sensing components (not shown) could include conventional optical or electrical trigger elements that provide a signal indicating when an analyte with properties meeting certain criteria moves past a position along channel 14. Furthermore, it may be possible to include sensing components for electrical impedance spectroscopy (EIS) for electronic pathology rather than sensing differential resistance for bioparticle sizing.

A series of sensing components as in FIG. 1 makes it possible to obtain spectral information about moving particles or other objects in order to achieve orthogonal characterization and reliable identification. Characterization is orthogonal if sensing components obtain information about orthogonal characteristics of a moving object, such as by photosensing different ranges of photon energies; sensing components could also be suitable for different intensity ranges. By choosing suitable materials, it is possible to obtain spectral information for the entire range from the deep ultraviolet to the far infrared or even for frequencies in the THz range.

Analyzer 10 can be designed to perform multi-signal analysis for a specific application, whether high wavelength resolution or broadband detection is desired. The technique illustrated in FIG. 1 also takes advantage of the motion of object 16 with a geometry that enables long integration times without sacrificing throughput capacity. Highly sensitive optical characterization methods can be used, such as fluorescence spectroscopy (illustratively in more than one range of photon energies) and Raman spectroscopy. Sivaprakasam, V., Houston, A., Scotto, C., and Eversole, J., "Multiple UV Wavelength Excitation and Fluorescence of Bioaerosols", *Optics* Express, Vol. 12, No. 9 (2004), pp. 4457-4466, have shown that using different UV excitation ranges provides more specific information about an analyte. Also, the use of multi-signal analysis makes it possible to perform reagentless bioagent identification.

Each of sensing components 54, 56, 58, and 60 includes a respective one of ICs 64, 66, 68, and 70, features of which are described in greater detail below. In general, however, each of these ICs includes a photosensor array, and the sensing component includes a set of cells of the photosensor array. The set of cells photosenses photons within a range of photon energies; for example, the sets of cells in ICs 66 and 68 could photosense different ranges of photon energies in the visible to ultraviolet range, and, as noted above, the set of cells in IC 70 could photosense in the infrared. Furthermore, more than one IC, such as ICs 66 and 68, could photosense fluorescing photons that are in the same energy range, but that result from excitation at different wavelengths such as from different LED or laser light sources. As explained in greater detail below, the set of cells for each of sensing components 54, 56, 58 and 60 includes a subset of cells, each of which photosenses in a respective subrange, and the subranges of at least two of the cells are different from each other.

Subranges of photosensing are "different from each other" in a given application if, at the application's minimum photon proportion, the subranges produce distinguishable photosensing results when the application requires. For example, if two subranges are so similar that their photosensing results cannot be distinguished when required, they are not different from each other. It should be noted, however, that subranges that are different from each other can nonetheless overlap or one of them can include another.

As described in greater detail below, sensing components 56, 58, and 60 can each be implemented with any suitable excitation or illumination technique to cause emanation of light from objects. One such technique, for example, is enhanced light-target interaction, which can be accomplished by anti-resonant waveguide techniques or other suitable excitation techniques. Enhanced light-target interaction is especially important if analyzer 10 is characterizing single particles or low concentrations of biological or chemical agents. In general, an anti-resonant waveguide has a core region surrounded by a cladding layer with a higher refractive index than the core region. Where the core region is a fluid that contains an analyte, light can be guided within the fluid, permitting photonic interaction over an extended length of a channel such as channel 14. As illustrated in FIG. 1, ICs 66, 68, and 70 are therefore supported on spacers 72, providing a suitable gap between each IC and the respective portion of channel 14 to avoid interference with anti-resonant waveguiding.

Anti-resonant waveguide techniques are described in greater detail in co-pending U.S. patent application Ser. No. 10/976,434, entitled "Anti-resonant Waveguide Sensors" and incorporated herein by reference in its entirety. Additional techniques are described in Goddard, N. J., Singh, K., Bounaira, F., Holmes, R. J., Baldock, S. J., Pickering, L. W., Fielden, P. R., and Snook, R. D., "Anti-Resonant Reflecting Optical Waveguides (ARROWs) as Optimal Optical Detectors for MicroTAS Applications", dias.umist.ac.uk/NJG/Abstracts/MicroTAS/MicroTas2.htm, pp. 1-5, and Singh, K., and Goddard, N. J., "Leaky Arrow Waveguides for Optical Chemical and Biosensors", (Abstract Submitted to Biosensors 1998), dias.umist.ac.uk/NJG/Abstracts/Biosensors/ARROW-Biosensors.htm, pp. 1-2, both of which are incorporated herein by reference.

In optical biosensors, the interaction between light and target molecules is typically very weak. Techniques in which light propagates in a longitudinal direction, such as anti-resonant waveguide techniques, can improve the interaction because of the extended length in which interaction occurs. Also, such techniques are very suitable for multi-signal analysis because they are relatively unaffected by changes in wavelength or film thickness. More particularly, in contrast to excitation techniques that use evanescent fields of ordinary waveguides and therefore require very small channels, fluidic channels with maximum transverse dimensions as great as a few millimeters can be used as anti-resonant waveguides. Suitable configurations can include, for example, an aerosol in a glass capillary tube or a liquid film between glass slides. The excitation could be with visible light, ultraviolet light, infrared light, radiation in the terahertz range, or any other appropriate electromagnetic radiation. Examples of specific sensing components employing anti-resonant waveguide techniques are described in greater detail below.

The use of anti-resonant waveguides and other techniques for enhanced light-target interaction may require additional mechanisms to suppress background excitation light. The use of an anti-resonant waveguide, by itself, strongly reduces background detected by a photosensor array located parallel to the waveguide, as illustrated below. In addition, if each cell of a photosensor array is only photosensing a subrange of photon energies, additional background suppression occurs because other photon energies will not be photosensed; in some implementations, for example, they may be reflected from a coating over the photosensor array. Additional background suppression can be obtained using a wavelength filtering component as part of the wall of channel 14 or as an additional coating on top of a photosensor array.

FIG. 2 shows schematically a cross-section of analyzer 10 taken along the line 2-2 in FIG. 1. Although FIG. 2 therefore shows features of second fluorescence component 58, similar features would be found in first fluorescence sensing component 56 and, to an extent, in Raman scatter sensing component 60.

As object 16 travels through portion 80 of channel 14 in the downstream direction indicated by arrow 82, it receives light from an excitation component, illustratively light source 84 which could be a laser or an LED, for example; in general, excitation radiation in any of various different energy ranges can be coupled into channel 14 to produce anti-resonant waveguiding. Portion 80 can function as an anti-resonant waveguide in response to light from source 84, or it can function in another way that provides enhanced light-target interaction. For example, other techniques that provide continuous excitation to a fluorescing molecule include tracking the molecule in motion with a scanning laser beam; using a linear array of LEDs to sustain particle excitation along its path; arranging a collimated beam along the particle path without waveguiding; and providing a Fabry-Perot-style cavity in which light passes through the medium containing the particle several times.

Sensing components using anti-resonant waveguide modes are especially advantageous in combination with fluidic devices because the fluidic channels themselves can be used as anti-resonant waveguides in various configurations. Examples of configurations include an aerosol carrying analytes in a capillary, a liquid film carrying analytes within a channel or between glass slides, etc.

In response to light from source 84, an analyte within object 16 fluoresces, emitting light with a characteristic spectrum of photon energies. A portion 86 of the light is emitted toward assembly 87, which includes at least IC 68 and possibly also other structures. Photons in portion 86 can therefore be photosensed by cells of a photosensor array on IC 68. Assembly 87 is positioned so that the photosensor array on IC 68 is close to and parallel to the path of object 16 through portion 80, to increase light collection efficiency.

The term "emanation path" or simply "path" is used herein to refer to a substantially continuous series of positions from which light may emanate, with a part of a path being referred to herein as a "segment". Segments may overlap or be included, one in another. Photon emanation along a path "can vary" if it is possible for total quantities of photons emanated from different positions along the path to be measurably different.

A photosensor array is "positioned along" or "along" a path or a segment if the array is positioned near the path or segment in such a way that one or more of its photosensors can photosense light emanating from the path or segment.

Assembly 87 is illustratively supported on spacers 72 to avoid disturbing anti-resonant waveguiding in portion 80 of channel 14. Spacers 72 are positioned outside portion 80, and, as a result, air gap 88 below assembly 87 prevents disturbance of waveguiding because air has a lower refractive index than that of the liquid within the waveguide. Any other appropriate structure could be provided that would prevent disturbance of waveguiding; examples include a gas or vacuum layer or possibly even a liquid layer or film with a low refractive index. A thin gap, layer, or film that is only a few microns thick, e.g. 10 µm, is sufficient to prevent disturbance of waveguiding if it has a sufficiently low refractive index.

Because object 16 receives excitation continuously throughout portion 80, fluorescence also occurs continuously along the photosensor array. As a result, spectral information is collected continuously as object 16 moves through portion 80. As described below, a similar technique can be used for light scattered by object 16.

The structure shown in FIG. 2 could also be used to implement Raman scatter sensing component 60 in a way that, although not comparable to dedicated Raman sensors, may provide acceptable performance and resolution with sufficient spectral range for a given application such as for specific Raman bands of interest. The output signal could indicate a set of intensity ratios of selected Raman lines and/or certain narrow intervals of a Raman spectrum rather than a complete Raman spectrum. By focusing on key differentiators in a Raman spectrum, this technique could provide the most relevant input for data analysis and comparison against a library of Raman profiles or another such database. This approach may be more tractable and efficient as a first step than comparing an entire Raman spectrum with a huge library of profiles.

To implement a Raman scatter sensing component as shown in FIG. 2, it would be necessary that light source 84 and IC 68 meet appropriate specifications, especially with regard to sensitivity and background light suppression within analyzer 10. In addition, suitable optical elements would be necessary between channel 14 and the photosensor array of IC 68 to ensure efficient and suitable light sampling.

Exemplary differences between a fluorescence sensing component and a Raman scatter sensing component would be as follows: A fluorescence sensing component could include a photosensor array in which cells photosense within a wide spectral range with rather low resolution, e.g. 400-700 nm with a moderate wavelength resolution of 2-5 nm. In contrast, a Raman scatter sensing component could include a photosensor array in which cells photosense within a smaller spectral range close to the excitation wavelength but with greater resolution, e.g. 800-830 nm with a resolution of 0.2-0.5 nm or even higher resolution. The sensing range for Raman scatter sensing must be set in accordance with typical energies of Raman scattered photons, which are 100 cm$^{-1}$ to a few 1000 cm$^{-1}$ wavenumbers different from the excitation photon energy, where wavenumber k=$2\pi/\lambda$ in units of 1/cm.

FIG. 2 also illustrates one of the ways in which support structure 12 could be implemented. Support layer 90 could, for example, be a light-transmissive glass or silicon substrate. Channel 14 can be defined in a micromolded layer 92 of polydimethylsiloxane (PDMS). PDMS is an inexpensive, biocompatible, transparent, silicon based elastomer with controllable hardness, hydrophobicity, excellent gas permeability, and surface chemistries that can be tuned to specific applications. It is sufficiently transparent in the visible portion of the spectrum to allow visualization of fluidic transport and measurements through a portion of layer 92, such as by a photosensor array on IC 68. In patterning layer 92 and other layers in FIG. 2, the length of channel 14 in which light-target interaction occurs can be chosen to minimize interference between different analytes.

Techniques for producing a patterned layer of PDMS are described, for example, in Becker, H., and Gartner, C., *Electrophoresis*, Vol. 21, 2000, p. 12, incorporated herein by reference. For example, a template can be fabricated on glass from SU-8 polymer, and PDMS can then be deposited to form a patterned structure within the template. The template can then be removed. Over layer 92 is a plate 94, such as glass and therefore another example of a light-transmissive structure.

The use of a patterned layer of PDMS is merely illustrative, however. A wide variety of other techniques could be used to produce microchannels or other channels suitable for analyzer 10. For example, techniques could be used that etch glass to produce channels. Also, channels could be microfabricated by patterning a layer of a polymer material such as SU-8 to produce high aspect ratio channel walls. Depending on the medium that carries analyte through channel 14, parameters of channel 14 can be modified for optimal results. If the medium is an ordinary fluid, for example, the optimal width of the channel will be different than if the medium is an aerosol. It may also be necessary to adjust the width of the channel to obtain a desired throughput.

A specific parameter of channel 14 that can have significant effects is adhesiveness of the channel wall. For example, experiments with *B. Thurengiensis* on uncoated surfaces have shown that adhesion may be a concern. This would be especially important for microfluidic channels, i.e. channels with maximum transverse inner dimensions less than 0.1 mm—their characteristically high surface area to volume ratio could lead to significant system loss. Bioadhesion could also compromise the ability to track the passage of a sample analyte through the entire length of channel 14. Bioparticles are attracted to charged or highly polarized surfaces such as glass, plexiglass acrylic, silicon, and even polymeric materials. With prolonged contact, bacteria and proteins may adhere to almost any surface by exposing more of their hydrophobic core regions, thus adapting their contact area to the specific surface properties. Once such a molecule is sufficiently close (e.g. 1-10 nm) to any surface, van der Waal's force dominates, and adhesion becomes a significant issue.

Various techniques can be used to reduce sample loss through surface adhesion, such as by providing barriers that prevent bioparticles from coming too close to the surfaces. More specifically, an anti-adhesive coating can be applied to prevent bioparticles and other analytes from sticking to the walls. Dip-coated polyethylene glycol (PEG) is a good choice for preventing adhesion of most biomaterials such as bacteria and proteins. In addition, PEG may be very well suited for microfluidic devices, since PEG can maintain capillary force on aqueous solutions. Other coatings may be viable options depending on sample properties, material interface chemistry, and operating conditions and regimes; for example, parylene C or vapor deposited tetraglyme might provide appropriate coatings. As noted above, anti-resonant waveguiding techniques can employ a channel with an inner diameter at least up to approximately 1.0 mm and possibly greater, in which case adhesion is not as great a problem and clogging is unlikely to occur; nevertheless, anti-adhesion measures may be advantageous to prevent spurious background signals emitted by material adhering to a channel's inner wall.

FIG. 2 also shows optical component 96 on the side of support layer 90 opposite PDMS layer 92. Optical component 96 provides an appropriate surface 98 through which light from source 84 can be coupled into the anti-resonant waveguide within portion 80 of channel 14. Although shown as separate layers in FIG. 2, support layer 90 and optical component 96 could instead be fabricated from a single layer of material by suitable processes.

FIG. 3 is a schematic view of an implementation of assembly 87 in which IC 68 includes photosensor array 100 and also has spacers 72 attached to it, such as after microfabrication of array 100 and other components. Photosensor array 100 is illustratively a two-dimensional array, with at least two rows of cells that include photosensors.

Different rows or other parts of photosensor array 100 can be provided with different coatings or can be otherwise structured so that their cells photosense different ranges or subranges of photon energies. As a result, the information obtained from a single IC can provide a detailed analysis of incident photons over a broad range of photon energies. In addition, reference cells, such as the cells in row 102, can be used to provide a spatially resolved real-time reference signal, such as to continuously monitor position of an object emanating light as it moves past array 100.

Within an array, a "pair" of cells is any two cells; unless otherwise specified, the cells in a pair need not have any other specific relationship to each other. The cells in a pair are "near each other" if the distance between them meets a suitable criterion for nearness, such as being no greater than ten times the maximum diameter of the larger of the cells. In general, for example, two cells that are adjacent are also near each other. More generally, a set of cells are all "nearby" another cell if each cell in the set and the other cell, taken as a pair, are near each other. A feature of array 100 is that it includes one or more reference cells that are nearby to a subrange cell, such as by being adjacent to the subrange cell.

Each cell in row 102 photosenses photons throughout a suitable range, characterized as $\lambda_{all}$, to produce a reference for a nearby cell in row 104. For implementations in which it is advantageous to have signal strengths of the same order from a cell in row 102 and its paired cell in row 104, the cell in row 102 must be different from the cells in row 104. For example, it could have a different sensing area or it could have a gray filter coating different than a coating over the paired cell in row 104.

Each cell in row 104, on the other hand, photosenses a respective subrange between $\lambda_{min}$ and $\lambda_{max}$, with illustrative cell 106 photosensing a subrange centered around $\lambda_p$. IC 68 also includes array circuitry (not shown) as well as peripheral circuitry 110 which perform various functions relating to readout of photosensed information from array 100.

One advantage of the technique illustrated in FIG. 3 is that IC 68 provides a compact photosensor array that can be used for various functions within a system such as analyzer 10. The compactness of IC 68 also allows for an interactive detection scheme. Subsequent or adjacent ICs within analyzer 10 may exchange information or trigger events. The combination of analysis results from several ICs within analyzer 10 may help to obtain orthogonal information and ultimately enable reliable identification of object 16.

Figure 4:
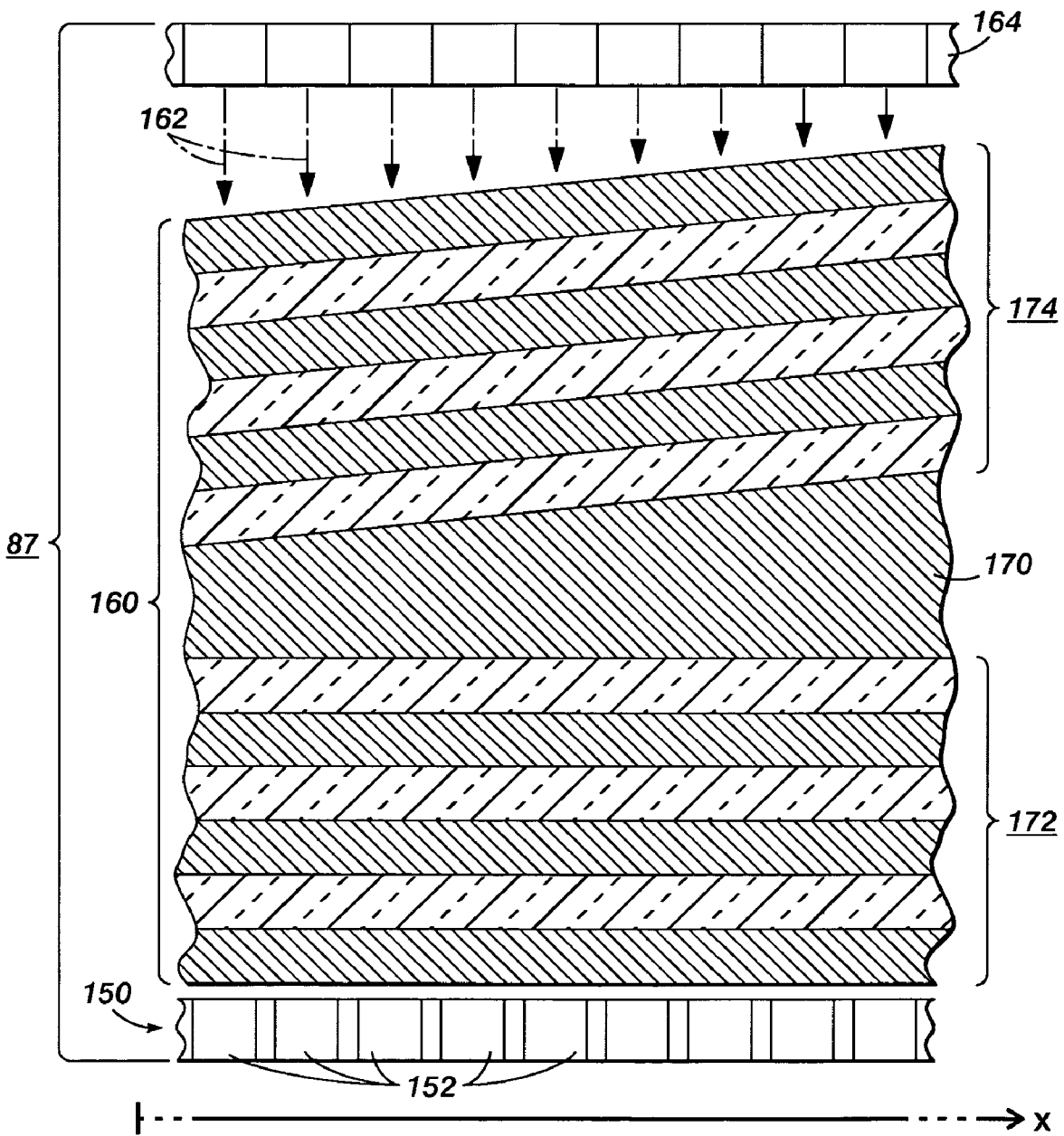
FIG. 4 is a schematic cross-sectional view of another implementation of an assembly that can be used in FIG. 2.

FIG. 4 illustrates another implementation of assembly 87, showing in greater detail how cells of an array photosense subranges, such as in row 104 in FIG. 3. As in FIG. 2, assembly 87 as in FIG. 4 can be supported over air gap 88 by spacers 72.

In FIG. 4, a cross-section has been taken through a fragment 150 of a photosensor array, with cells 152 of the fragment 150 shown schematically in cross-section. Over cells 152 is a transmission structure 160 that receives incident light 162, such as from an optional Selfoc® or other gradient index (GRIN) lens array, illustrated by lens array portion 164. Lens array portion 164 can be designed to receive light from air gap 88 as in FIG. 2 and to provide a parallel beam to structure 160, increasing spectral resolution.

A structure that "transmits" photons, sometimes referred to herein as a "transmission structure", is any material structure through which light can propagate. It is not necessary that there be a one-to-one relationship between photons that enter a transmission structure and photons that exit from it as long as the structure provides exiting photons in response to entering photons as a result of light propagation through the structure.

More generally, to "transmit" photons is to perform a function by which exiting photons at an exit position are provided in response to entering photons at an entry position as a result of light propagation between the entry and exit positions. To "transmit only" a specified set of photons from a first position to a second refers to a function that transmits photons from the first position to the second, but predominantly photons in the specified set. As with photosensing, described above, if a transmission structure transmits only a specified set of photons, between 60-90% of the transmitted photons are in the specified set, but the percentage could be lower or higher. In some applications, 90% or even 95% or more of the photons are in the specified set.

One type of transmission structure is a "coating", meaning a layered structure of light-transmissive material that is on or over another component such as a photosensor array. A coating varies "continuously" along a scan path or other path if the coating varies as a continuous function of its position along the path.

A transmission structure provides (and a cell receives from a transmission structure) photons "throughout", "within", or "in" a range or subrange if the provided photons are predominantly within the range or subrange. As with photosensing, described above, between 60-90% of the photons from a transmission structure typically have energies within the range or subrange, but the percentage could be lower or higher. In some applications, 90% or even 95% or more of the photons have energies within the range or subrange.

Transmission structure 160 can, for example, be a film with laterally varying light transmission properties as described, for example, in co-pending U.S. patent application Ser. No. 10/922,870, entitled "Chip-size Wavelength Detector" and incorporated herein by reference in its entirety. In the portion of transmission structure 160 shown in FIG. 4, wedge-shaped transmissive cavity 170 is enclosed between reflective films 172 and 174, forming a wedge-shaped Fabry-Perot etalon. Because its thickness varies as a function of position along the x-axis, transmission structure 160 will transmit different wavelengths as a function of position along the x-axis.

Transmission structure 160 can be produced with appropriate coatings on or over a photosensor array. Films 172 and 174 and cavity 170 could all be produced, for example, by exposure to deposition beams in an evaporation chamber; films 172 and 174 with uniform thicknesses could be produced by appropriate on-axis deposition, while cavity 170 with laterally varying thickness can be produced by appropriate off-axis deposition. FIG. 4 illustratively shows films 172 and 174 as relatively thick compared to cavity 170, which would be appropriate for layers of non-metallic material such as $SiO_2$, $TiO_2$, or $Ta_2O_5$, with thicknesses designed as described below; such materials are typically used to produce Bragg mirrors by depositing thin alternating layers with low absorption coefficients and large differences in refractive indices. If films 172 and 174 are reflective metal, however, they could be much thinner.

For an implementation with non-metallic material, specific thicknesses of cavity 170 and films 172 and 174 could be designed from the desired transmitted wavelength λ and the refractive index n of cavity 170. The thickness of cavity 170 is typically chosen to be $\lambda/(2n)$ or an integer multiple thereof, while the thicknesses of Bragg mirror layers within films 172 and 174 are typically $\lambda/(4n)$. The number of pairs of such layers in each of films 172 and 174 can vary between a few (e.g. 2-5) all the way up to 20 or 30, depending on the difference in refractive index between the two materials used, the desired transmission band width, and the desired stop band reflectivity. Therefore, in typical implementations, films 172 and 174 are much thicker than cavity 170, as suggested in FIG. 4.

Figure 5:
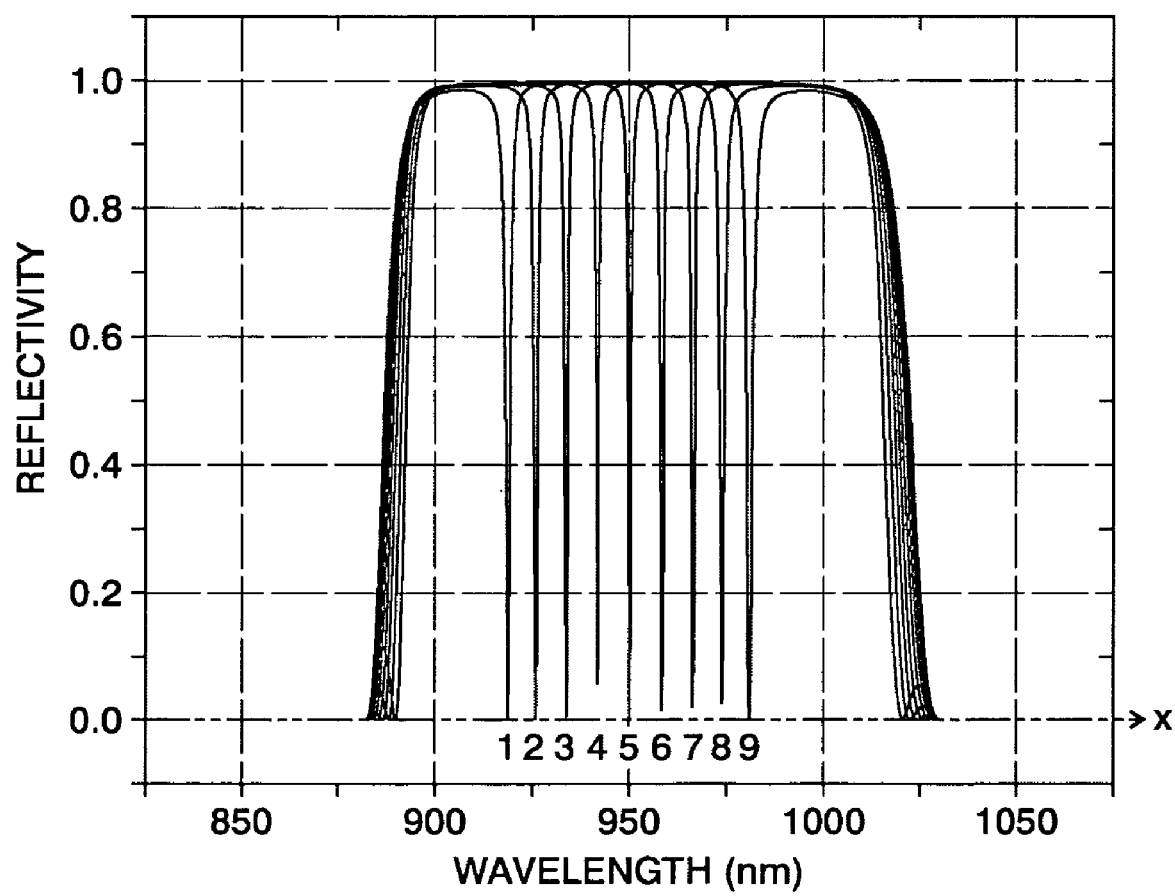
FIG. 5 is a graph illustrating laterally varying light transmission properties of a transmission structure in FIG. 4.

FIG. 5 illustrates the laterally varying light transmission properties of transmission structure 160. Because its thickness varies as a function of position along the x-axis, cavity 170 transmits different wavelengths as a function of position along the x-axis. Wavelengths of photons predominantly transmitted to nine of cells 152 as in fragment 150 are illustrated by the low reflectivity minima labeled 1 through 9. As can be seen, the high-transmissivity photon energy range for transmission structure 160 varies laterally.

Figure 6:
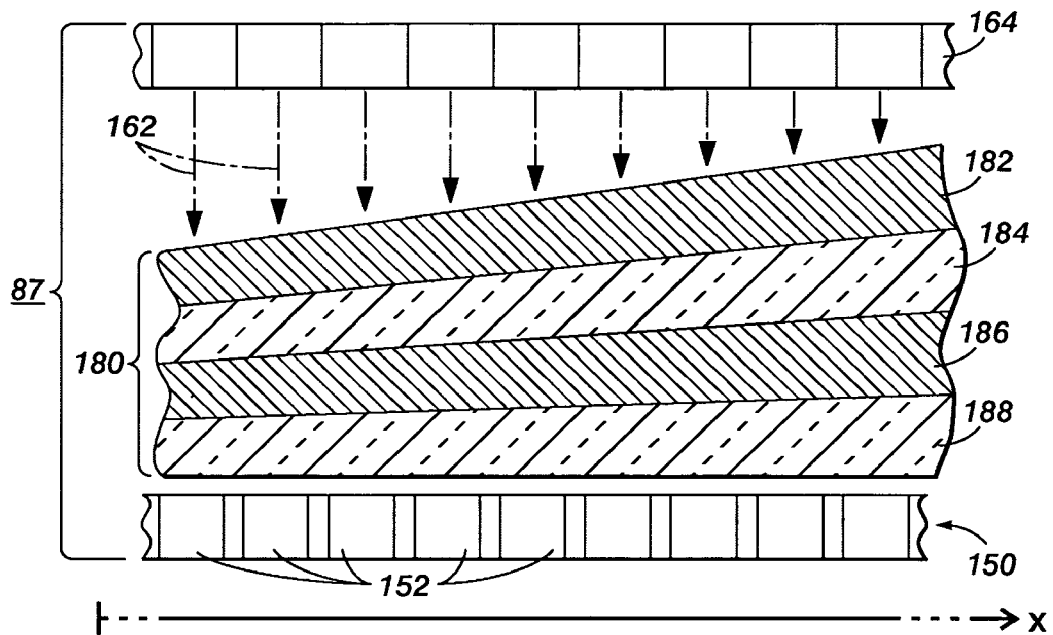
FIG. 6 is a schematic cross-sectional view of another implementation of an assembly that can be used in FIG. 2.

FIG. 6 illustrates another implementation of assembly 87, with features that have the same reference numbers as in FIG. 4 being implemented as described above. Rather than transmission structure 160, however, assembly 87 includes transmission structure 180. Transmission structure 180 can, for example, be a laterally graded Bragg mirror in which each of layers 182, 184, 186, and 188 is laterally graded. Each of layers 182, 184, 186, and 188 could be produced as described above for cavity 170, using off-axis deposition in an evaporation chamber.

Figure 7:
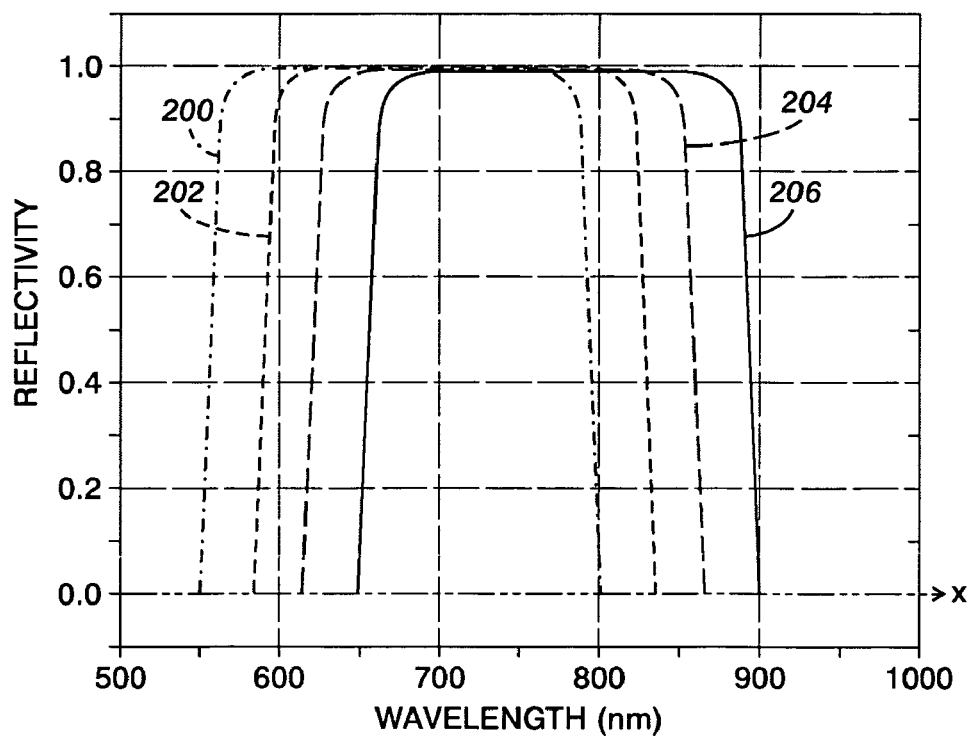
FIG. 7 is a graph illustrating the laterally varying light transmission properties of a transmission structure in FIG. 6.

FIG. 7 illustrates the laterally varying light transmission properties of transmission structure 180. Because its thickness varies as a function of position along the x-axis, transmission structure 180 reflects different wavelengths as a function of position along the x-axis. Curves 200, 202, 204, and 206 are shown, representing reflectivity of the portion of transmission structure 180 over each of four cells 152 in fragment 150, with curve 200 being for the leftmost cell of the four in FIG. 6 and curve 206 being for the rightmost cell of the four. As can be seen, the high-reflectivity photon energy range for transmission structure 180 varies laterally.

Figure 8:
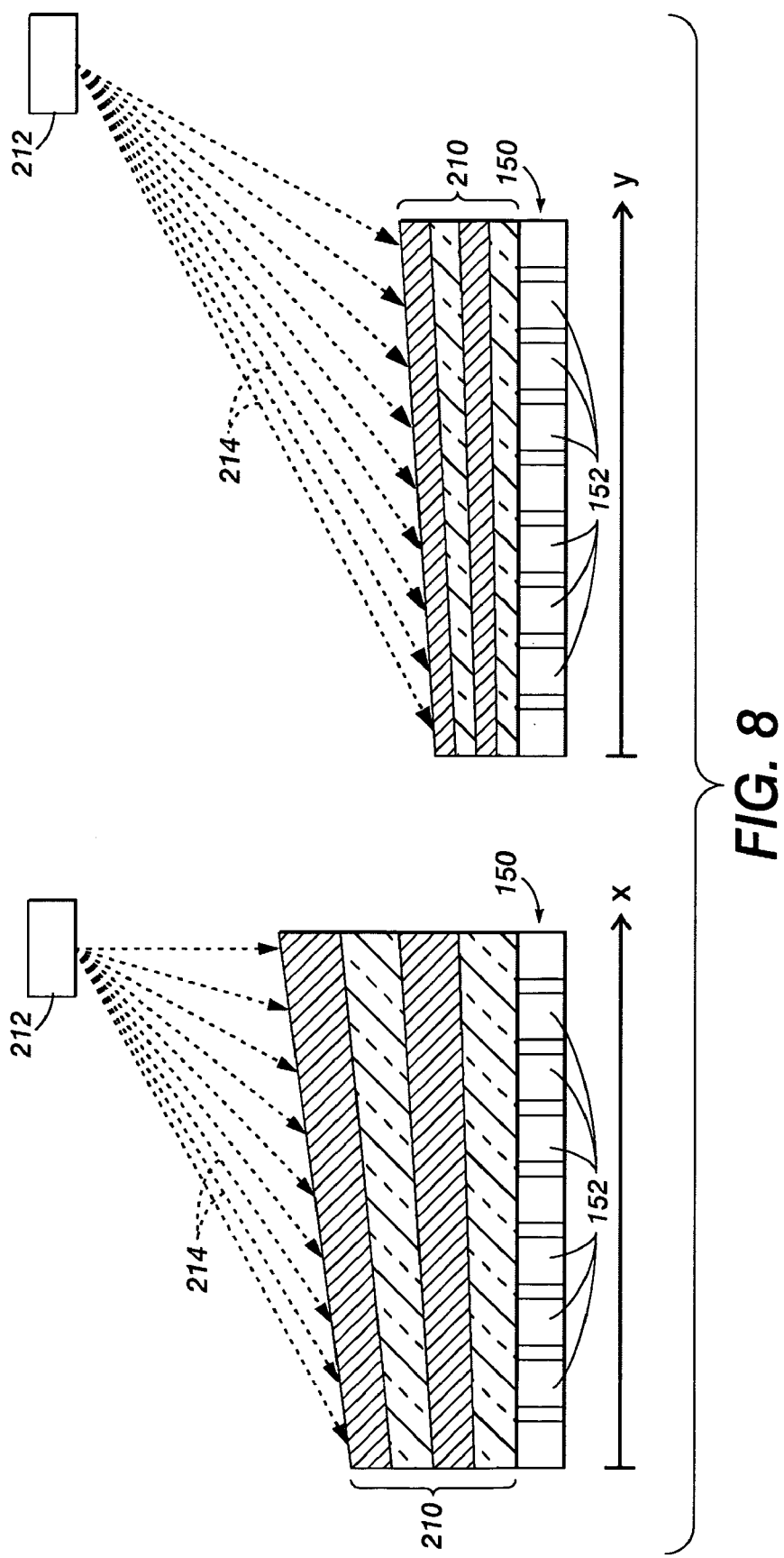
FIG. 8 illustrates a technique that produces a transmission structure that can be used in an assembly as in FIG. 2, showing orthogonal schematic cross-section views of deposition.

FIG. 8 illustrates a technique that produces transmission structure 210 with laterally varying light transmission properties similar to those illustrated in FIGS. 5 and 7 but with lateral variation in each of two dimensions. This technique can be used to produce different coatings for different rows of a photosensor array so that their cells photosense different ranges or subranges of photon energies, and can be used separately or in combination with reference cells.

Transmission structure 210 is produced on or over cells 152 of photosensor array 150 by using deposition source 212 to provide deposition beam 214 that can be characterized at any given point on the surface of structure 210 by two angles. One of the two angles results from angular variation of deposition beam 214 in the x-direction across array 150, while the other results from angular variation in the y-direction. As a result, the thickness gradient of structure 210 is similarly different in the x- and y-directions. Therefore, cells within each row extending in one of the two directions will photosense a range of photon energies similarly to FIG. 7, but the range will be different than the range photosensed by cells in any other row extending in the same direction.

The technique of FIG. 8 could be implemented in a variety of ways. For example, during deposition, structure 210 could be formed on a support structure that is tilted as required, deposition source 212 could be tilted as required, or both kinds of tilt could be employed.

Figure 9:
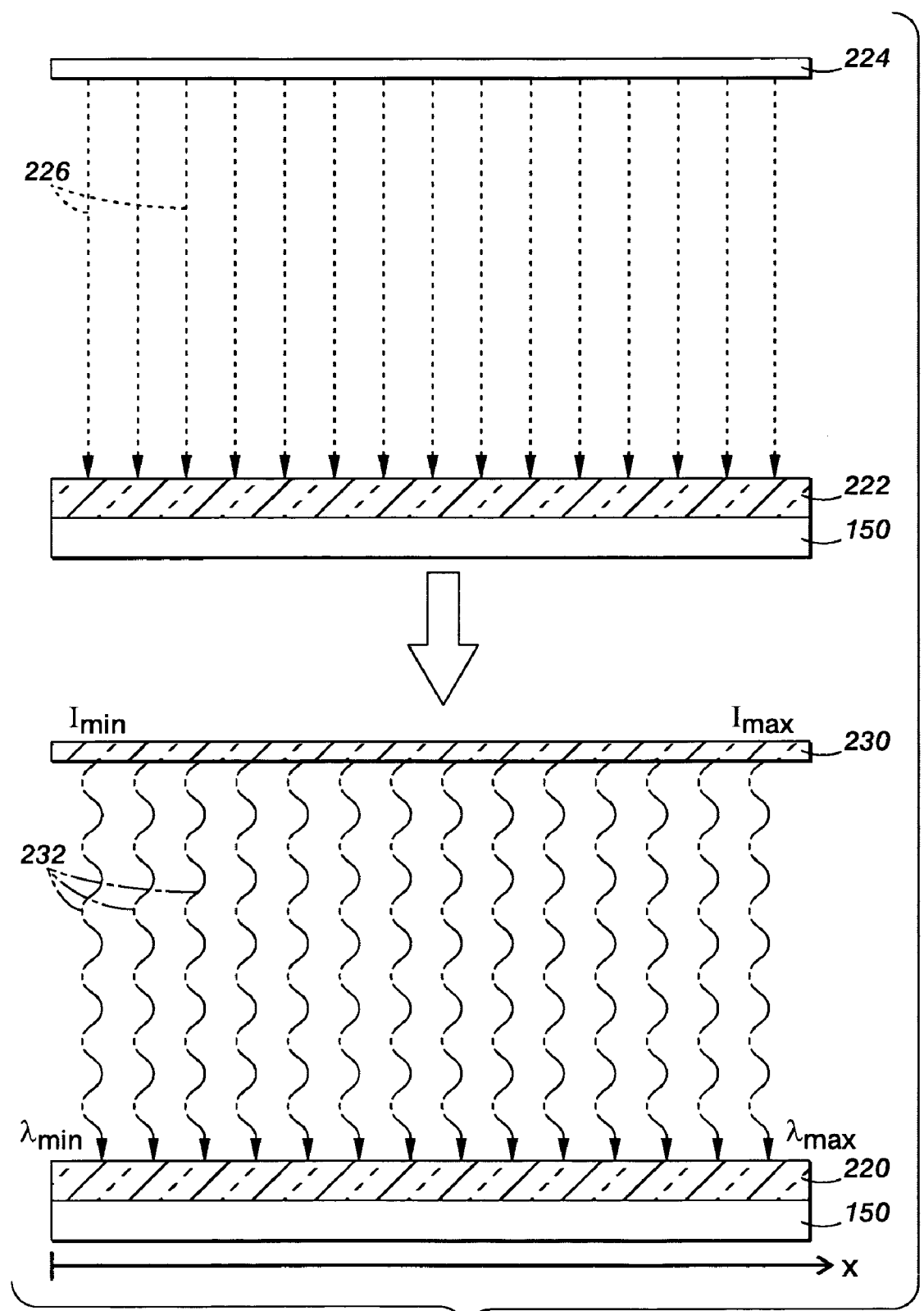
FIG. 9 illustrates another technique for producing a transmission structure that can be used in an assembly in FIG. 2, showing two schematic cross-section views of stages of the technique.

FIG. 9 illustrates a technique that produces transmission structure 220 with laterally varying light transmission properties similar to those illustrated in FIGS. 5 and 7 but without variation in thickness of transmission structure 220. The technique in FIG. 9 can be characterized as providing laterally varying optical thickness d*n, where d is thickness and n is index of refraction, but without actual variation in thickness d. In contrast, the techniques of FIGS. 4-8 provide varying optical thickness by providing actual variation in thickness.

In the upper part of FIG. 9, homogeneous coating 222 is deposited by deposition source 224, which provides deposition beam 226 uniformly over the surface of photosensor array 150 similar to those in FIGS. 4, 6, and 8. This operation could, for example, be implemented with conventional deposition techniques.

Then, in the lower part of FIG. 9, light source 230 provides radiation 232 that is scanned across the coating over array 150 to introduce a laterally varying change of refractive index in resulting transmission structure 220. For example, source 230 can be an ultraviolet source that provides intensity I with a constant value along each line parallel to the y-axis (perpendicular to the plane of FIG. 9), but varying from $I_{min}$ for lines nearer the y-axis to $I_{max}$ for lines farther from the y-axis, as shown in FIG. 9 by the values along the x-axis. As a result, the wavelengths transmitted to cells in array 150 can vary along the x-axis from $\lambda_{min}$ to $\lambda_{max}$, as shown. The same pattern of intensity can be concurrently applied by source 230 to each of a number of arrays that are appropriately arranged, allowing batch fabrication of arrays. Two-dimensional variation in optical density equivalent to that in FIG. 8 could also be obtained with two-dimensional variation in the ultraviolet source's intensity.

The techniques illustrated in FIGS. 4-9 could be implemented in various other ways, with different cells of a photosensor array photosensing slightly different subranges of a range of photon energies. For example, additional details about various production and calibration techniques and characteristics of transmission structures that could be employed are described in co-pending U.S. patent application Ser. No. 10/922,870, entitled "Chip-size Wavelength Detector" and incorporated herein by reference. Also, co-pending U.S. patent application Ser. No. 11/316,241, entitled "Photosensing to Obtain Information From Photon Energies" and incorporated herein by reference, describes a step-like transmission structure that could be used.

The implementations in FIGS. 3-9 illustrate examples of photon energy sensors that include an IC and a transmission structure. The IC includes a photosensor array, and within the array are lines of cells. First and second lines include pairs of cells that are near each other. The transmission structure, over the second line of cells, provides incident photons to cells in the second line. For at least one of the pairs, the cell in the second line receives incident photons within a respective subrange of an application's energy range from the transmission structure, while the paired cell in the first line receives incident photon substantially throughout the application's energy range.

The implementations of manufacturing techniques described above in relation to FIGS. 4-9 also illustrate methods of producing photon energy sensors that include an IC and a transmission structure as described above.

If quantities photosensed by the cells are read out in parallel, spectral information about incident photons is obtained. As illustrated in FIG. 3, nearby cells, such as in a parallel row, can photosense quantities of photons throughout the range of photon energies to provide reference information. If adjacent cells in the array have overlapping subranges, computational techniques such as deconvolution can be used to improve accuracy.

In general, the resolution of a technique as in any of FIGS. 4-9 depends heavily on the number of cells in an array, the full width half maximum (FWHM) of the transmission peak, and the peak shift per cell. The smaller the FWHM and the peak shift, the better the resolution. On the other hand, the totally covered spectral width can be enhanced by increasing the FWHM and the peak shift per cell. Therefore, the technique can be customized to the needs of a specific application. For example, the use of a Fabry-Perot cavity as in FIG. 4 enables very high spectral resolution, while a version with multiple cavities and many layers as in commercially available products will be favorable for applications with low light intensities in combination with small spectral resolution such as with fluorescence. With such an approach, the spectral width of the transmission window and the reflectivity of the stop band can be optimized separately, which may be advantageous because the reflectivity of the stop band determines stray light suppression. It would also be possible to use a single laterally graded distributed Bragg reflector (DBR) mirror as in FIGS. 6 and 7 to obtain a photosensor array with high light sensitivity but limited wavelength resolution, appropriate for fluorescence or luminescence sensing.

In a version with only one DBR mirror with slightly graded transmission properties as in FIGS. 6-8, integrated over a photodiode array for example, the photocurrent in each cell is slightly different from its neighbors depending on the incident light spectrum. If the transmission properties of the DBR over each cell are known, the original spectrum of incident light can be reconstructed. The number of cells defines the number of spectral points that can be reconstructed and therefore determines spectral resolution. The reconstruction works best for wavelengths where transmission changes drastically from one cell to the next. Therefore, this technique could be used to resolve wavelengths at the edges of the DBR mirror. The DBR mirror could be positioned in such a way that the side edges on one side cover the spectral region being analyzed. Multiplication of the resulting photocurrent with a matrix that contains the transmission function of the DBR mirror provides a reconstruction of the incident light spectral distribution.

Resolution can be improved by positioning DBRs on a second row of the photodiode array so that the opposite edge of the reflectivity plateau overlaps the spectral range of interest. Once again, to evaluate the data, the total light intensity distribution must be known for all cells, which can be obtained from a third row of pixels without any DBRs.

A particular advantage of analyzer 10, when implemented with techniques similar to those of FIGS. 3-9, is that spectral information of objects can be collected step-by-step as the objects move across or along a series of sensing components, each of which obtains information about a respective range of photon energies. As a result, highly sensitive optical characterization techniques can be combined, including multiple range fluorescence spectroscopy and Raman spectroscopy, as described above in relation to FIG. 1. Each of sensing components 56, 58, and 60 can be thought of as a chip-size spectrometer that includes a photosensor array together with a laterally varying filter such as a coating. The laterally varying transmission and reflection properties of the coating over the photosensor array define a correlation between position and photon energy. Therefore the spatially dependent signal from the photosensor array contains information about the incident spectrum. Because of the distributed nature of the spectrometer and the fact that the incident light traverses the photosensor array in the process of resolving spectral distribution, sensitivity is improved, making additional optics unnecessary.

Relative movement between an object and a photosensor array can be obtained in various ways, such as by moving one or both of the object and the array. Movement of an object can be guided in various ways, including by falling through a funnel under gravitational acceleration; by being injected into a well-defined stream of air, liquid, or other particles; or by being guided by a tube, capillary, or similar aperture. In general, high sensitivity is obtained by the above techniques because the light from the object is received at any given time by only a few cells with relatively narrow subranges. But by photosensing light emanating from an object or another optical signal across the entire array, information about a complete range of photon energies can obtained. This technique therefore allows longer integration times than conventional techniques but does not sacrifice throughput capacity. Sensitivity can be adjusted by selecting the size and number of cells assigned to a specific subrange of photon energies. Simpler optics can be used and no dispersion element is necessary. Note that in conventional spectrometers, any light that is diffracted into the $0^{th}$, $2^{nd}$, and higher orders is wasted.

In experimental implementations, a coating as in FIG. 4 typically transmits approximately 60% of photons in its respective subrange. The subranges can be chosen with wavelengths that span between 0.01 and tens of nanometers (nm), depending on the design and gradient of the coating and the cell size of the photosensor array. Very high light yield can be achieved by using a highly sensitive photosensor, such as an avalanche photosensor array.

In contrast to transmission structures 160, 180, 210, and 220, any coating or other transmission structure over row 102 in FIG. 3 must function as a gray filter across the range $\lambda_{all}$ in order to provide a suitable reference. It may also be possible to leave row 102 uncoated in some implementations.

Figure 10:
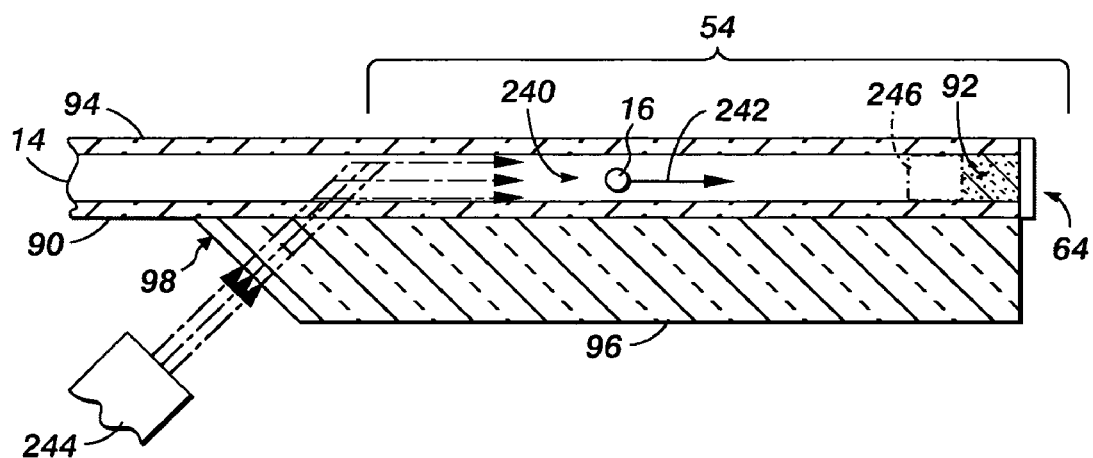
FIG. 10 is a schematic cross-sectional view of the analyzer in FIG. 1 taken along the line 10-10.

FIG. 10 shows schematically a cross-section of analyzer 10 taken along the line X-X in FIG. 1. FIG. 10 therefore shows several features of optical absorption sensing component 54, including IC 64, which is shown by itself, but would be implemented within an assembly, such as any of the implementations of assembly 87 as described above.

As object 16 travels through portion 240 of channel 14 in the downstream direction indicated by arrow 242, it receives light from an excitation component, illustratively light source 244 which is a suitable broadband illumination component such as a white light source and which could be an LED or a halogen lamp. As in FIG. 2, portion 240 can function as an anti-resonant waveguide in response to light from source 244, or it can function in another way that provides enhanced light-target interaction, as described above.

In response to light from source 244, object 16 scatters or absorbs light, resulting in a modified spectral distribution of transmitted light photosensed by cells of a photosensor array on IC 64. For example, object 16 may contain an analyte that absorbs photons within certain energy subranges, producing an absorption spectral distribution. Because object 16 receives excitation continuously throughout portion 240, cells on IC 64 will continue to photosense the absorption spectral distribution as object 16 passes through portion 240 of channel 14. Then, the spectral distribution will return to its unmodified form when object 16 exits from sensing component 54 through curved portion 246 of channel 14.

Figure 11:
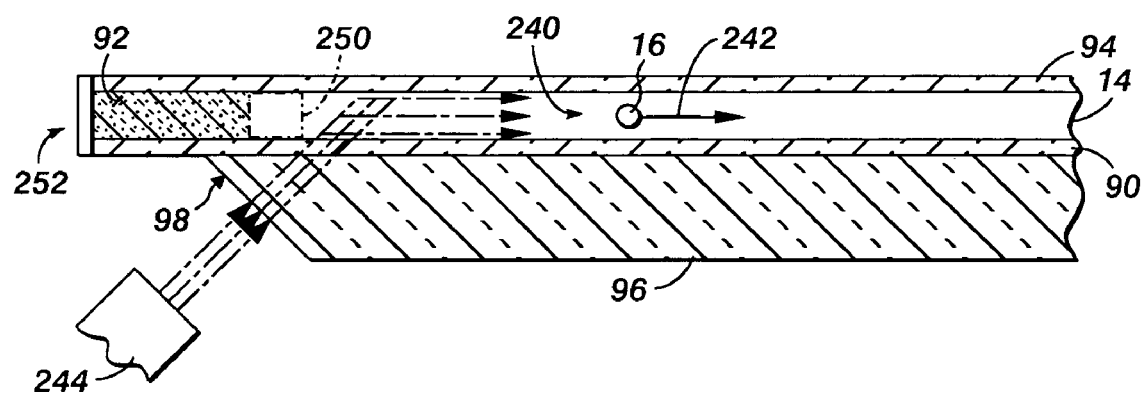
FIG. 11 is a schematic cross-sectional view similar to that of FIG. 10 for a backscatter sensing component.

FIG. 11 shows schematically a cross-section of analyzer 10 taken along a line similar to that of FIG. 10 but through a Raman backscatter sensing component. As suggested by the reference numerals that are the same as in FIG. 10, many features of FIG. 11 are implemented the same as in component 54. For example after entering through curved portion 250 of channel 14, object 16 travels through portion 240 in the downstream direction indicated by arrow 242 and receives light from an excitation component, illustratively light source 244 as in FIG. 10. Portion 240 can function to provide enhanced light-target interaction, as described above.

In response to light from source 244, object 16 (or an analyte in it) performs Raman scattering of light in an upstream direction, referred to herein as backscattering. The backscattering results in a modified spectral distribution photosensed by cells of a photosensor array on an IC within assembly 252, illustratively positioned at the upstream end of portion 240 of channel 14, but alternatively positioned outside the downstream end if source 244 illuminates portion 240 from the downstream end. Assembly 252 could be implemented with any appropriate structure, including the above-described implementations of assembly 87. Because object 16 receives excitation continuously throughout portion 240, cells on the IC in assembly 252 will continue to photosense the backscattered spectral distribution as object 16 passes through portion 240 of channel 14. Then, the spectral distribution will return to its unmodified form as object 16 exits from the sensing component.

IC 64 and the IC in assembly 252 could each be implemented with the techniques described above in relation to FIGS. 3-9. For example, cells in row 102 of photosensor array 100 could provide reference information for use in correcting position-dependent inhomogeneities resulting from characteristics of channel 14. As shown, the photosensor array of the IC in assembly 252 covers the whole end facet of channel 14, including the channel walls; this is necessary because backscattered light may not only propagate freely through liquid in channel 14 but may also be guided within the walls surrounding the liquid, such as in layer 90 and plate 94.

FIG. 12 illustrates exemplary operations in producing a transmission structure. In use, a photosensor array under the transmission structure includes both reference cells that photosense substantially throughout an application's photon energy range and also includes subrange photosensing cells ("subrange cells") that photosense within respective subranges of the application's photon energy range. Signals indicating quantities of photons sensed by subrange cells can be adjusted based on quantities of photons sensed by reference cells, as described in greater detail below.

An operation produces a signal indicating a first quantity of photons "adjusted based on" a second quantity of photons if the signal's value depends on the first and second quantities in accordance with a function that approximates the first quantity but modifies it in a way that depends on the second quantity. For example, if the second quantity is a quantity of photons throughout an application's energy range and the first quantity is a quantity of photons in a subrange, the function could normalize the first quantity based on the second quantity. Normalization is only one suitable type of function, however—a first quantity could be adjusted based on a second quantity in accordance with any of a wide variety of other functions.

To make it possible to adjust quantities of photons based on reference quantities, the operations illustrated in FIG. 12 could be used, for example, to produce a suitable transmission structure for photosensor array 100 in FIG. 3, in which row 102 includes reference cells and row 104 includes subrange cells. Additional examples in which the technique of FIG. 12 could be used are described below.

The operation in box 300 in FIG. 12 produces a coating for the reference cells. The coating could be produced directly on a photosensor array or it could be produced on a light transmissive substrate that is later positioned over the photosensor array. In one technique, for example, a mask could be produced photolithographically in which only reference cell areas are exposed; a uniform coating for the reference cells could then be deposited over the mask, such as by e-beam deposition of dielectric multi-layer structures or thin metal films, and a liftoff operation could be performed to remove the mask and coating from nonexposed areas. In another technique, a homogeneous coating could be deposited on the photosensor array or on the light transmissive substrate, and subsequent operations as described below could begin with the homogeneous coating; in this case, deposition could similarly be performed by e-beam deposition of dielectric multi-layer structures or thin metal films.

The operations in boxes 302, 304, and 306 then produce coatings for subrange cells. The operation in box 302 produces a mask in which a subset of the subrange cells is exposed. As described above in relation to box 300, this operation could be performed photolithographically.

The operation in box 304 then deposits additional layers over the mask. For example, if the operation in box 300 produced a uniform coating only over reference cells, with other regions uncoated, the operation in box 302 can deposit a wedge-shaped coating or other coating with laterally varying optical thickness, such as by e-beam deposition of dielectric multi-layer structures or thin metal films, as described, for example, in co-pending U.S. patent application Ser. No. 10/922,870, incorporated herein by reference in its entirety. On the other hand, if the operation in box 300 produced a homogeneous coating over all cells, the operation in box 304 can first deposit a wedge-shaped coating or other coating with laterally varying optical thickness and can then deposit another homogeneous coating. The lower and upper homogeneous coatings can function as mirrors above and below a cavity provided by the coating with laterally varying optical thickness.

After the operation in box 304 is completed, the operation in box 306 then removes the coating or coatings from box 302 from all areas except the exposed subrange cells described in relation to box 302. This could be done, for example, by a liftoff operation removing the mask produced in box 302 together with the coating material deposited over it. As suggested by the dashed line from box 306 to box 302, the operations in boxes 302, 304, and 306 could then be performed for another subset of subrange cells until all subrange cells have been appropriately coated.

The operation in box 310 completes assembly, performing any necessary alignment and mounting of the coating to the IC that includes the photosensor array, for example. In addition, the operation in box 310 includes adding connectors and any other circuitry for communication between circuitry on the IC and external circuitry. In addition, the operation in box 310 could include addition of a housing over or around the IC with the coatings.

The technique of FIG. 12 could be modified in many ways within the scope of the invention. Furthermore, the technique of FIG. 12 is extremely general, and could be employed to produce a wide variety of different arrangements of reference cells and subrange cells. The example illustrated in FIG. 3, above, includes adjacent rows of cells in which a subrange cell in one row has an adjacent paired reference cell in the other row. In this example, the quantity photosensed by a cell in row 104, $I_{subrange}$, can be normalized based on the quantity photosensed by its paired reference cell cell, $I_{ref}$, such as by a simple computation of the ratio $I_{subrange}/I_{ref}=I_{norm}$. This approach could be followed whether the reference cells are coated as described above in relation to FIG. 12 or, on the other hand, are uncoated. In either case, normalization can be performed within a subset of the subrange cells if all of their paired reference cells have approximately the same sensing area and the same amount of attenuation of incident light, where the attenuation is independent of photon energy, as would be the case if gray filtering is performed. Another advantage of gray filtering is that it can produce signals with similar values in the reference cells as compared to the subrange cells by reducing intensity by a factor such as 10 or 100; gray filtering thus facilitates operations on signals and avoids problems like CCD overflow.

Implementations of FIG. 12 thus illustrate examples of methods that produce a photon energy sensor that includes an IC and a transmission structure. The IC includes a photosensor array, and within the array are lines of cells. First and second lines include pairs of cells that are near each other. The transmission structure, over the second line of cells, provides incident photons to cells in the second line. For at least one of the pairs, the cell in the second line receives incident photons within a respective subrange of an application's energy range from the transmission structure, while the paired cell in the first line receives incident photon substantially throughout the application's energy range.

In specific implementations, the method that produces the sensor can deposit a second line coating over the second line of cells, and the transmission structure can include the second line coating. The method can also deposit a first line coating over the first line of cells, and the first line coating can provide incident photons substantially throughout an application's energy range to the first line of cells.

Figure 14:
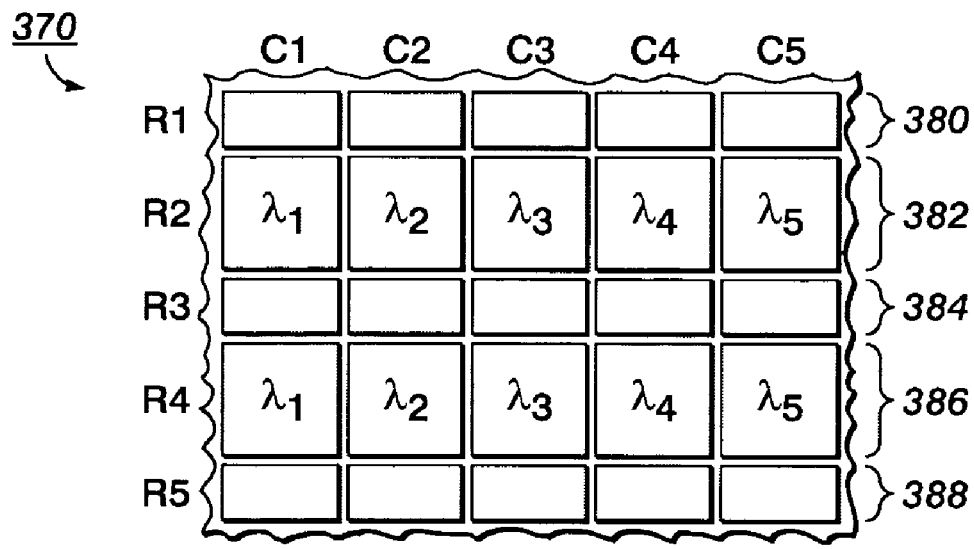
FIG. 14 is a schematic plan view of a segment of another photosensor array that could be used in an assembly as in FIG. 2.
Figure 15:
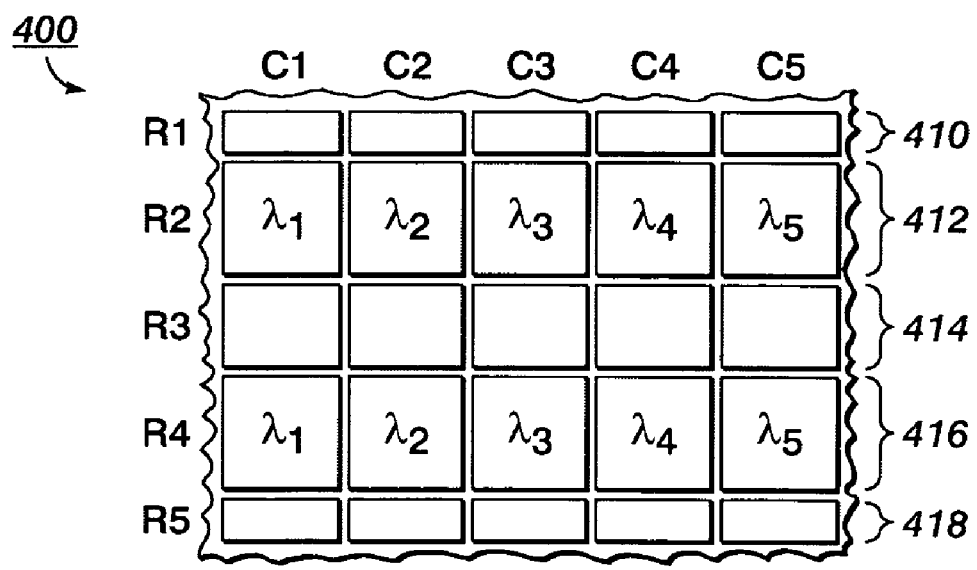
FIG. 15 is a schematic plan view of a segment of another photosensor array that could be used in an assembly as in FIG. 2.

FIGS. 13-15 illustrate other arrangements of subrange and reference cells that make it possible to perform various other normalizations in addition to the simple normalization technique described above. In each of these figures, subrange cells are labeled with a wavelength $\lambda_n$, while reference cells are not labeled with a wavelength. Also, in general, subrange cells in each column have the same subrange, although an implementation as in FIG. 8 could produce cells with different subranges within a column.

The implementations in FIGS. 13-15 are described in terms of "rows" and "columns" (with rows and columns labeled, such as R1 and C1), but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

Array segment 330 in FIG. 13 illustratively includes portions of five rows (R1-R5) 340, 342, 344, 346, and 348, and five columns (C1-C5) 350, 352, 354, 356, and 358. Cells in rows 340, 344, and 348 are reference cells that photosense substantially throughout the application's photon energy range; as noted above, these reference cells could be coated with a wavelength independent attenuation filter or could be uncoated. In contrast, rows 342 and 346 include subrange cells, each of which photosenses a respective subrange of the application's photon energy range, and the subranges of different cells in each of rows 342 and 346 are different from each other.

Array segment 330 illustrates an example in which a line of reference cells, specifically row 344, is between two lines of subrange cells, specifically rows 342 and 346. Furthermore, array segment 330 illustrates two examples in which lines of subrange cells, specifically rows 342 and 346, are each between two lines of reference cells; specifically, row 342 is between rows 340 and 344, while row 346 is between rows 344 and 348. In the illustrated example, all of the cells have substantially the same sensing area.

Array segment 370 in FIG. 14 is similar to array segment 330 in that rows 380, 384, and 388 include reference cells, while rows 382 and 386 include subrange cells. As can be seen, however, the sensing area of each reference cell in rows 380, 384, and 388 is substantially smaller than the sensing areas of each subrange cell in rows 382 and 386. This technique can be used to adjust the quantities of photosensed photons in the cells so that quantities sensed in the reference cells and in the subrange cells are roughly equal in magnitude. The specific ratio of sensing areas of reference cells to subrange cells can be chosen in accordance with the application, taking into account the low intensity incident on the subrange cells because of light reflected by the transmission structure.

In the examples in FIGS. 13 and 14, the quantity $I_{i,j}$, photosensed by a subrange cell at row i and column j, can be normalized in various ways based on quantities photosensed by nearby reference cells. The normalized intensity $I_{norm(r,c)}$ for a cell at row r (i.e. any of rows 342, 346, 382, or 386) and column c could be calculated using any of the following expressions, some of which would also be applicable to the implementation in FIG. 3:

$$\frac{I_{r,c}}{I_{(r-1),c}}, \frac{I_{r,c}}{I_{(r+1),c}}, \frac{2 \cdot I_{r,c}}{I_{(r-1),c} + I_{(r+1),c}}, \frac{6 \cdot I_{r,c}}{\sum_{j=c-1}^{c+1}(I_{(r-1),j} + I_{(r+1),j})}.$$

These expressions are merely exemplary, and various other normalizations or other appropriate adjustments could be performed based on quantities of photons sensed by reference cells.

Array segment 400 in FIG. 15 is similar to array segments 330 and 370 in that rows 410, 414, and 418 include reference cells, while rows 412 and 416 include subrange cells. As in array 370, the sensing area of each reference cell in rows 410, 414, and 418 is substantially smaller than the sensing area of each subrange cell in rows 412 and 416. On the other hand, the sensing area of each reference cell in rows 410 and 418 is also substantially smaller than the sensing area of each reference cell in row 414, with the sensing area of each cell in row 414 illustratively being approximately twice the sensing area of each reference cell in rows 410 and 418. In this example, the normalized intensity $I_{norm(r,c)}$ can be calculated, for example, using any of the following expressions:

$$\frac{I_{r,c}}{I_{(r-1),c}}, \frac{I_{r,c}}{I_{(r+1),c}}, \frac{3 \cdot I_{2,c}}{2 \cdot I_{1,c} + I_{3,c}}, \frac{3 \cdot I_{4,c}}{2 \cdot I_{5,c} + I_{3,c}},$$

where the first and second expressions are appropriate for subrange cells in either of rows 412 and 416 but the third and fourth expressions are only appropriate for subrange cells in row 412 and row 416, respectively.

Figure 16:
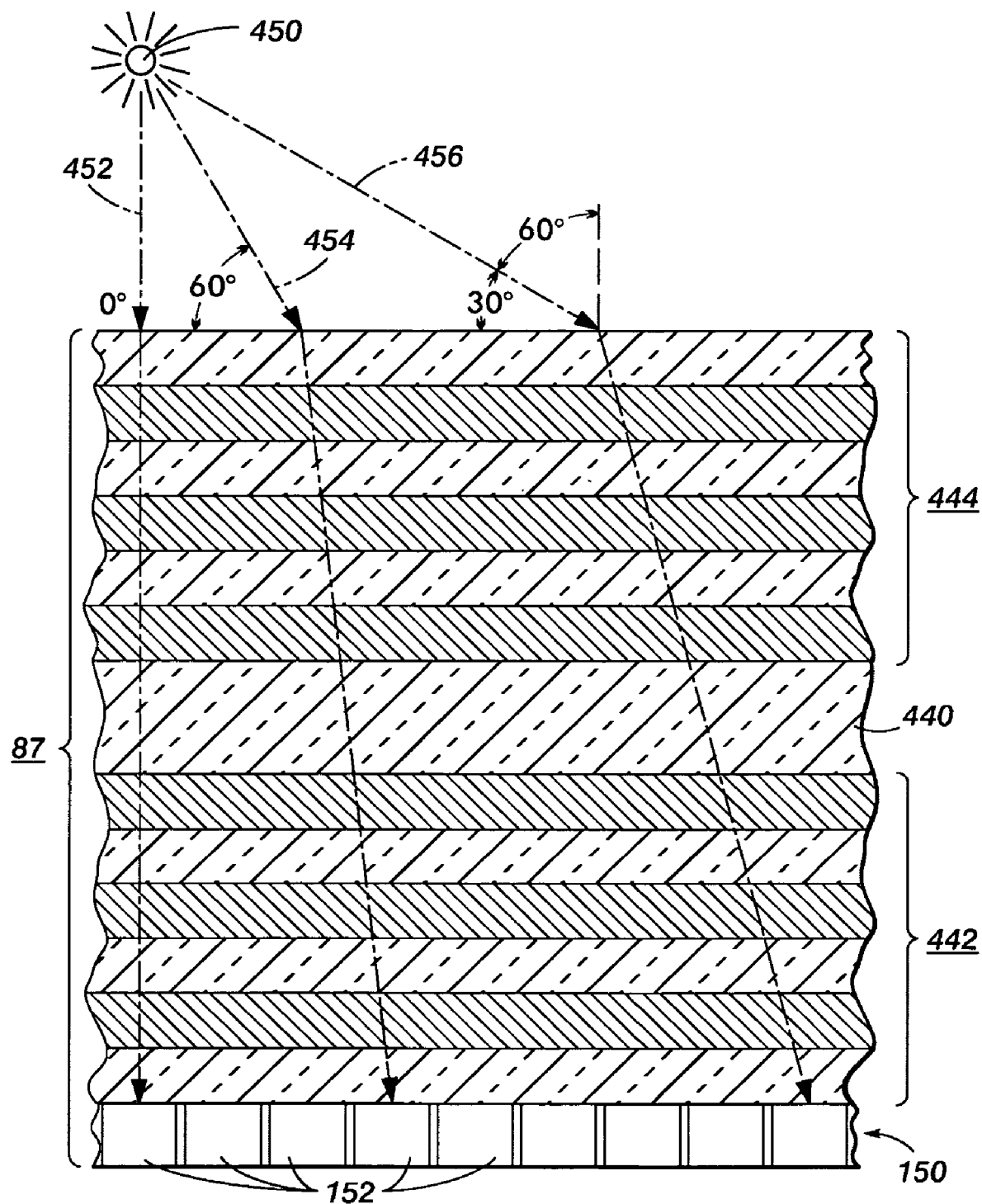
FIG. 16 is a schematic cross-sectional of another assembly similar to those that could be used in FIG. 2.

Although the subrange differences in rows 342, 346, 382, 386, 412, and 416 in FIGS. 13-15 could be produced with any of the techniques described above in relation to FIGS. 4-9, various other techniques might also be used. FIG. 16 illustrates an example in which photosensor array 150 would include uncoated or gray-filtered reference cells (not shown) and subrange cells that receive incident light from a homogeneous Fabry-Perot cavity 440 between DBR mirrors 442 and 444. Cavity 440 and mirrors 442 and 444 could be produced as described above in relation, e.g., to FIGS. 4 and 12, but without lateral variation in transmission characteristics. Cells 152 photosense different subranges because the transmission and reflection properties of mirrors 442 and 444 depend on the angle of incidence of light. In other words, each subrange cell is, in effect, illuminated at a different angle of incidence, so that the characteristics of the transmission structure preceding it differ from that of adjacent cells.

In this example, light source 450 can be a point- or slit-like source positioned over assembly 87. Three exemplary rays are shown in FIG. 16. Ray 452 has an angle of incidence of 0° from the normal and therefore passes straight through the transmission structure to the left-most subrange cell shown. Ray 454, in contrast, has an angle of incidence of 30° with the normal (i.e. an angle of 60° with the surface as shown), and ray 456 has an angle of 60° with the normal, so that each of these rays follows a longer path through the transmission structure than the path of ray 452. The resulting graph of reflectivity as a function of wavelength would resemble FIG. 5, with photons of a certain energy illuminating only one or a few subrange cells, corresponding to a range of angles of incidence.

Implementations as in FIGS. 13-16 thus illustrate examples of photon energy sensors that include an IC and a transmission structure. The IC includes a photosensor array, and within the array are lines of cells. First and second lines include pairs of cells that are near each other. The transmission structure, over the second line of cells, provides incident photons to cells in the second line. For at least one of the pairs, the cell in the second line receives incident photons within a respective subrange of an application's energy range from the transmission structure, while the paired cell in the first line receives incident photon substantially throughout the application's energy range.

Figure 17:
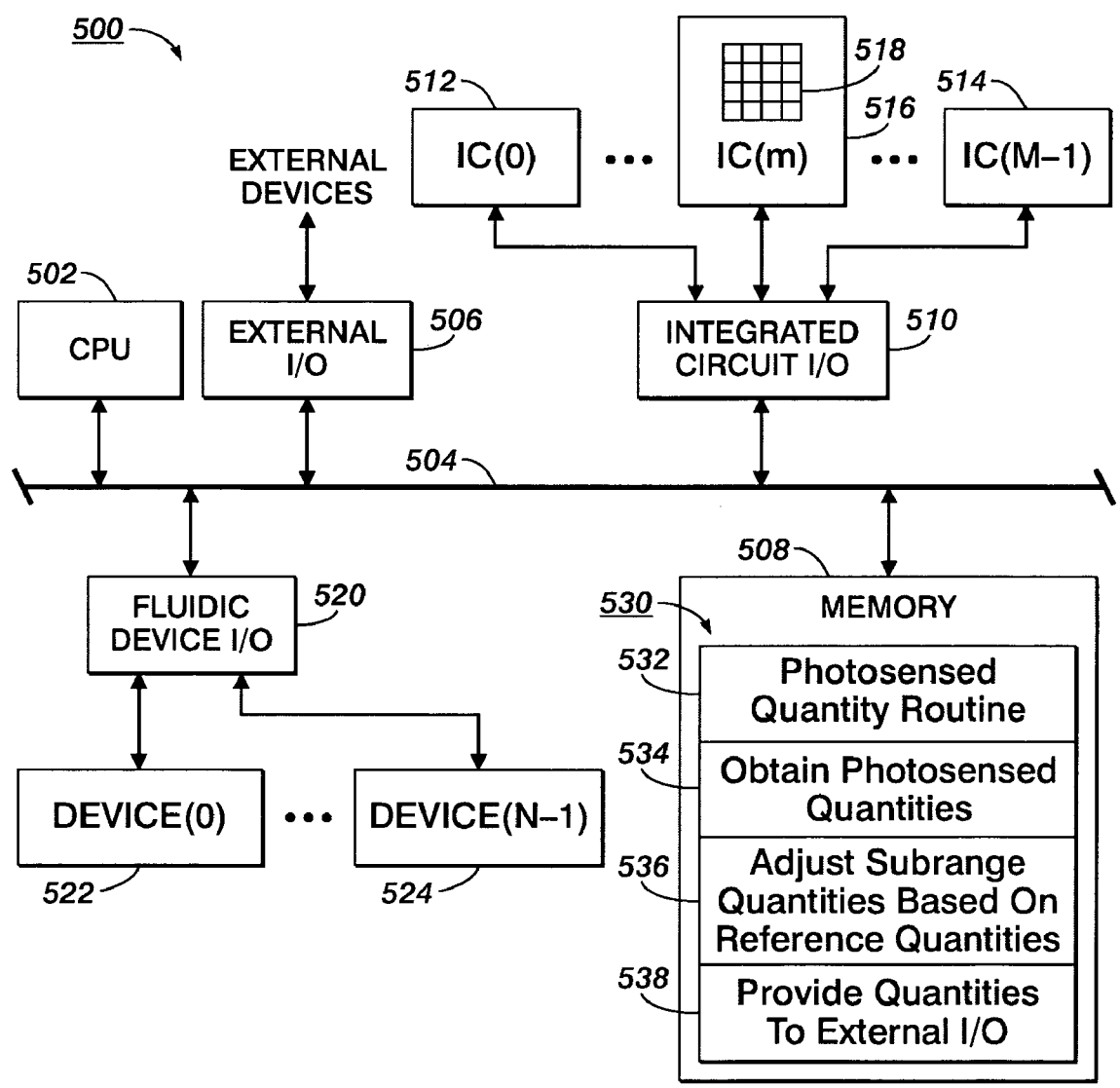
FIG. 17 is a schematic block diagram of a system that can control the analyzer in FIG. 1.

FIG. 17 illustrates system 500, an exemplary system that could be used to operate analyzer 10. Although system 500 illustratively includes central processing unit (CPU) 502 connected to various components through bus 504, a wide variety of other architectures could be employed, including any appropriate combination of hardware and software, as well as specialized hardware components such as application specific integrated circuits (ASICs) for one or more of the illustrated components or in place of a software component executed by CPU 502.

System 500 also includes external input/output (I/O) component 506 and memory 508, both connected to bus 504. External I/O 506 permits CPU 502 to communicate with devices outside of system 500.

Additional components connected to bus 504 are within or connected to analyzer 10. In the illustrated implementation of system 500, IC I/O 510 is a component that permits CPU 502 to communicate with ICs in analyzer 10, such as the various ICs' photodetectors, and other components described above; M ICs are illustrated in FIG. 17 by a series extending from IC(0) 512 to IC (M-1) 514. ICs 512 through 514 illustratively include IC(m) 516 with a photosensor array 518, which includes subrange cells and reference cells as described above. Similarly, fluidic device I/O 520 is a component permitting CPU 502 to communicate with various fluidic devices such as pumps, metering electrodes, smart gates and other devices for gating and bifurcating, valves, flow or pressure sensors, and so forth; N fluidic devices are represented in FIG. 17 by device (0) 522 through device (N-1) 524.

Memory 508 illustratively includes program memory 530 although instructions for execution by CPU 502 could be provided in various other forms of software or hardware, on or off of CPU 502. The routines stored in program memory 530 illustratively include photosensed quantity routine 532. When executed, routine 532 illustratively makes calls to subroutines 534, 536, and 538, which could instead be within routine 532. Subroutine 534 obtains photosensed quantities from subrange cells and reference cells, and could be implemented in any suitable manner for retrieving signals from IC(m) 516 or other ICs. Subroutine 536 can be called to adjust a quantity from a subrange cell based on quantities from one or more nearby reference cells, such as using one of the techniques described above in relation to FIGS. 13-15. Subroutine 538 can be called to provide the unadjusted quantities from subroutine 534 or the adjusted quantities from subroutine 536 as output through external I/O 506.

In one modification of system 500, IC(m) 516 could include peripheral circuitry (as in FIG. 3) that could perform the functions of subroutines 534 and 536, so that CPU 502 could instead retrieve adjusted quantities directly from IC(m) 516. For example, the peripheral circuitry could include components that read out quantities from a subrange cell and a paired reference cell and provide the sensed quantities in analog form to a circuit with a differential amplifier to obtain an analog difference or ratio of the two. For this modification, CPU 502 could execute the subroutines shown in FIG. 17 in a different order: First, CPU 502 could execute subroutine 536, which would be modified to include a sensing period in which cells in a photosensor array perform photosensing, as well as the operation of adjusting subrange quantities using the peripheral circuitry. Then, CPU 502 would execute subroutine 534, obtaining the adjusted photosensed quantities from the array. Finally, CPU 502 could execute subroutine 538 in the same manner as described above.

The system in FIG. 17, however implemented, illustrates a system that senses photon energies in an application's energy range. The system includes an IC and also adjusting circuitry. The IC includes a photosensor array positioned along a path along which photon emanation can vary. The array includes, along each of a number of segments of the path, respective first and second sets of cells. The cells in the first set photosense substantially throughout the application's energy range, while the cells in the second set photosense only within a respective subrange, and the respective subrange of at least two of the segments are different from each other. The adjusting circuitry responds to cells in the array, using quantities photosensed by a segment's first and second sets of cells to produce signals indicating quantity of incident photons in the segment's respective subrange adjusted based on quantity of incident photons throughout the application's energy range.

When executed by CPU 502, the instructions in program memory 530 illustrate a method of sensing photon energies in an application's energy range. For a path along which photon emanation can vary, the method photosenses with an IC that includes a photosensor array. The act of photosensing includes, in each of a number of segments of the path, photosensing substantially throughout the application's energy range with a first set of cells and photosensing within a respective subrange with a second set of cells. The respective subranges of at least two of the segments are different from each other.

Figure 18:
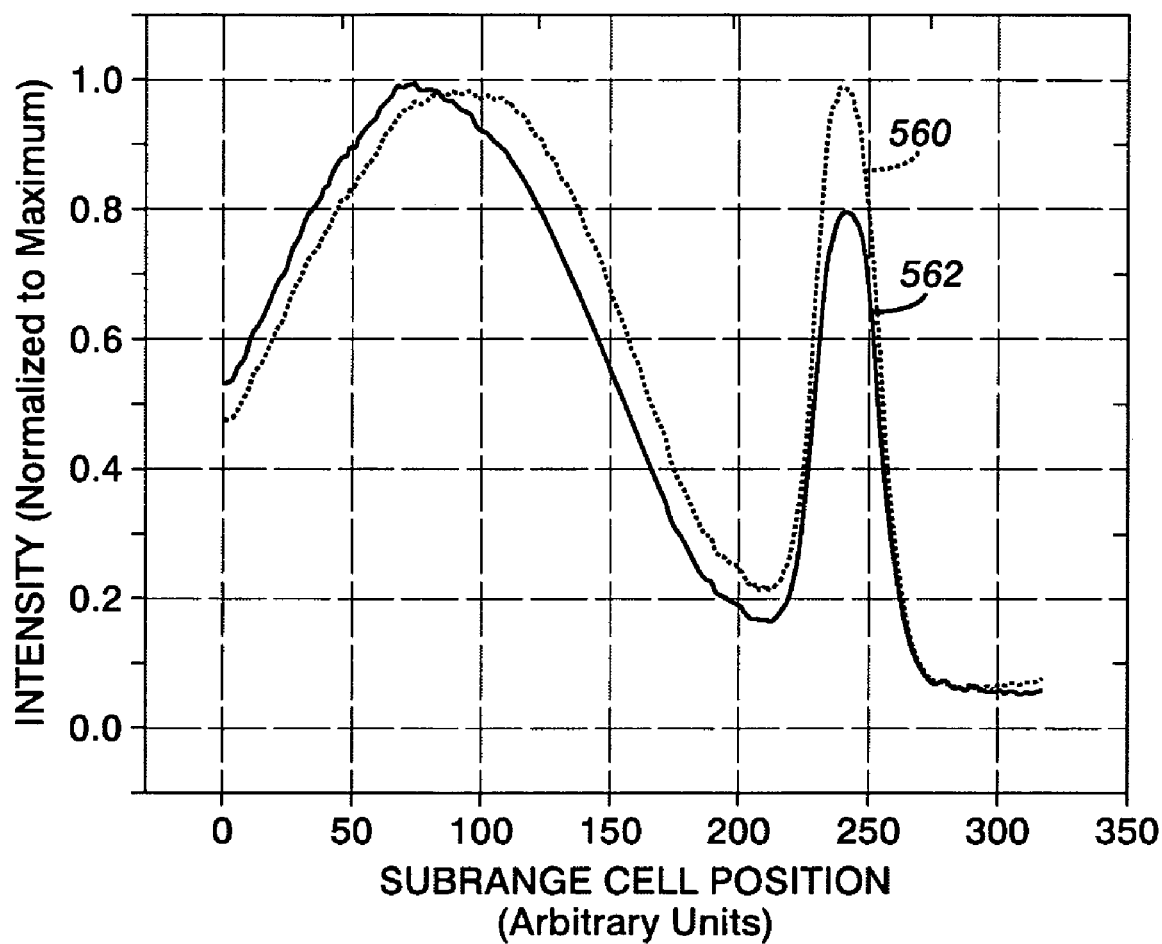
FIG. 18 is a graph illustrating output that could be provided by the central processing unit (CPU) of the system in FIG. 17.

FIG. 18 is a graph illustrating the relationship between the sensed quantities from subroutine 534 and the adjusted quantities from subroutine 536, both of which could be provided as output by subroutine 538. Curve 560 shows unadjusted intensity as a function of photon energy from a number of subrange cells. Curve 562 shows adjusted intensity as a function of photon energy, with the adjustment based on quantities photosensed by nearby reference cells. The values in curves 560 and 562 are illustrative only, but are a realistic example of values that could be obtained in practice.

Various of the techniques described above have been successfully implemented or simulated, including the production of a detector that includes a commercially available IC covered with a laterally graded Fabry-Perot cavity filter on a glass slide. Wavelength resolution has been experimentally determined and successfully simulated on a computer. Anti-resonant waveguide techniques have been successfully tested.

The exemplary implementations described above are advantageous because they can provide compact, inexpensive components that generally require no additional mechanical or optical parts to perform functions such as spectrometry. The results of photosensing can be read out rapidly and in parallel from a number of ICs. A number of ICs may be used to address a wide range of photon energies by using suitable coating materials, possibly ranging from the ultraviolet to the far infrared and even into the terahertz range. The ICs can be integrated into complex systems, such as fluidic systems, and may be employed for multiple functions, possibly including both spectrometry and wavelength shift detection. The ICs are especially useful in spectrometry applications in which light cannot be spread homogeneously over a photosensor array, because nearby reference cells can be used to normalize or otherwise adjust sensed quantities.

Spectrometry measurements have a wide variety of applications, including, for example, optical instrumentation, telecommunications, fluorescence devices, process control, optical signal scanning, detection systems for chemical and biological agents, and so forth. Various specific spectroscopic techniques can be implemented with the techniques described above, including absorption spectroscopy (e.g. gas sensing), fluorescence spectroscopy, and Raman spectroscopy, all of which are discussed above. The techniques described above, however, are not limited specifically to spectroscopy, but could also be applied in other photosensing situations. Additional description of applications in which photon energy is sensed in combination with relative motion is found in co-pending U.S. patent application Ser. No. 11/315,926, entitled "Sensing Photon Energies of Optical Signals", and U.S. patent application Ser. No. 11/315,386, entitled "Sensing Photon Energies Emanating from Channels or Moving Objects", both of which are incorporated herein by reference.

The exemplary implementations described above generally rely on transmission structures that include highly reflective interfaces, so that much of the incident light is reflected and only a small fraction reaches the photosensor array. Therefore, the techniques described above are especially useful in applications in which light intensity is very high or a light source emits through a large area or over an extended time. In addition, the above techniques make it possible to increase sensitivity by choosing very long integration times (without loss of throughput capacity), simpler optics, and no dispersion element. By contrast, some conventional systems such as monochromators lose all light defracted into the $0^{th}$, $2^{nd}$, and higher orders. In the implementations described above, very high light yield can be achieved by combining a transmission structure with a highly sensitive photosensor array, such as one that includes avalanche photodetectors.

In addition, components could have various shapes, dimensions, or other numerical or qualitative characteristics other than those illustrated and described above. For example, in the exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing the transmission structure and the cell sensing area; for example, the width may be as small as 0.1 nm or as great as tens of nanometers.

Some of the above exemplary implementations involve specific materials, such as in fluidic structures, photosensor arrays, and transmission structures, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information, whether based on CCD, CMOS, or other techniques. Various commercially available detector arrays have pixel densities as high as ten megapixels, and some high density ICs have become relatively inexpensive.

Similarly, transmission structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in transmission structures may vary from 30 nm up to a few hundred nanometers. Some of the above exemplary implementations involve particular types of transmission structures, such as Bragg mirrors and paired distributed Bragg reflectors separated by a Fabry-Perot cavity, but these transmission structures are merely exemplary, and any transmission structure that has laterally varying optical thickness could be used. Various techniques could be used to produce transmission structures with lateral variation in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Furthermore, various techniques other than transmission structures could be used to obtain photosensor arrays in which cells sense different subranges of photon energy.

Some of the above exemplary implementations employ an arrangement of ICs relative to fluidic structures in which fluid moves and may carry objects, and a wide variety of such arrangements, with or without fluidic structures, could be made within the scope of the invention. In one example, a preliminary inspection of an analyte could be made with an IC with a 400-700 nm laterally varying filter to detect fluorescence or scattering in the 400-700 nm range, after which a more refined inspection could be made with another IC, such as to perform Raman spectroscopy in the range of 100 $cm^{-1}$ to a few 1000 $cm^{-1}$. Rather than using separate ICs, different rows of a single two-dimensional photosensor array on an IC could be differently coated to photosense in different ranges.

Some of the above exemplary implementations employing fluidic structures also employ enhanced light-target interaction to obtain fluorescence. In general, however, the techniques described above could also be used for self-emitting or auto-fluorescing objects such as particles. Furthermore, various types of fluorescence, photo-luminescence, chemo-fluorescence, inelastic scattering, and so forth could be employed. The technique of anti-resonant waveguiding, described above, is only one of many techniques that could be used for enhanced light-target interaction, and any such excitation technique could be applied continuously or intermittently along a path. Various parameters could be adjusted to obtain anti-resonant waveguiding, including the shape of quartz or glass surrounding the channel; a thinner structure is generally better, with a surface parallel to the channel generally being required. Additional description of excitation techniques is found in co-pending U.S. patent application Ser. No. 11/316,660, entitled "Providing Light to Channels or Portions" and incorporated herein by reference in its entirety. Additional description of applications in which photons from objects in channels are sensed is found in co-pending U.S. patent application Ser. No. 11/315,992, entitled "Sensing Photons From Objects in Channels", and U.S. patent application Ser. No. 11/315,386, entitled "Sensing Photon Energies Emanating from Channels or Moving Objects", both of which are incorporated herein by reference.

The exemplary implementation in FIG. 17 employs a CPU, which could be a microprocessor or any other appropriate component. Furthermore, as noted above, the adjustment of photosensed quantities could be done either digitally or with analog signals, and could be done either on the same IC as a photosensor array, on other components, or on a combination of the two, with any appropriate combination of software or hardware.

The above exemplary implementations generally involve production and use of photosensor arrays, ICs, transmission structures, fluidic structures, sensors, illumination techniques, optical components, and analyzers following particular operations, but different operations could be performed, the order of the operations could be modified, and additional operations could be added within the scope of the invention. For example, in implementations in which a transmission structure is on a separate substrate from a photosensor array, the transmission structure could be moved relative to the photosensor array between consecutive sensing operations. Also, readout of adjusted or unadjusted sensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of sensing photon energies in an application's energy range, the method comprising:
   for a path along which photon emanation can vary, photosensing with an IC that includes a photosensor array; the act of photosensing comprising, in each of two or more segments of the path:
      with a respective first set of one or more cells of the array, photosensing quantity of incident photons substantially throughout the application's energy range; with a respective second set of one or more cells in the array, photosensing quantity of incident photons within a respective subrange of the application's energy range;
   the respective subranges of at least two of the segments being different from each other.

2. The method of claim 1 in which the act of photosensing further comprises, for each photosensor in the first and second sets of at least one of the segments:
   photosensing incident photons during a respective sensing period for the photosensor; and
   obtaining a signal indicating quantity of incident photons received during the photosensor's sensing period.

3. The method of claim 2 in which the sensing periods of the photosensors in the first and second sets are approximately concurrent.

4. The method of claim 1, further comprising:
   for at least one of the segments, using the quantities photosensed by the segment's respective first and second sets of cells to produce signals indicating quantity of incident photons in the segment's subrange adjusted based on quantity of incident photons throughout the application's energy range.

5. The method of claim 4 in which the act of using photosensed quantities to produce signals includes normalization.

6. A system that senses photon energies in an application's energy range, the system comprising:
   an IC that includes a photosensor array, the array being positioned along a path along which photon emanation can vary; the array including, along each of two or more segments of the path:
      a respective first set of one or more cells that photosense quantity of incident photons substantially throughout the application's energy range; and
      a respective second set of one or more cells that photosense quantity of incident photons within a respective subrange of the application's energy range; the respective subranges of at least two of the segments being different from each other; and
   adjusting circuitry that responds to cells in the array and that, for at least one of the segments, uses the quantities photosensed by the segment's respective first and second sets of cells to produce signals indicating quantity of incident photons in the segment's respective subrange adjusted based on quantity of incident photons throughout the application's energy range.

7. The system of claim 6 in which the array includes first and second lines of cells extending along the path; the first line including each segment's first set of cells and the second line including each segment's second set of cells.

8. The system of claim 7 in which the first and second lines are both at least one of straight lines and adjacent lines.

9. The system of claim 6 in which the array is a CMOS array or a CCD array.

10. The system of claim 6 in which the IC includes array circuitry in the array and peripheral circuitry outside the array, the adjusting circuitry including at least part of the peripheral circuitry.

11. The system of claim 6, further comprising:
    external circuitry electrically connected to the IC; the adjusting circuitry including at least part of the external circuitry.

12. The system of claim 6 in which the adjusting circuitry performs normalization.

13. The system of claim 6 in which the respective second set of cells of one of the segments includes one cell and the respective first set of cells includes one, two, or six cells.

14. The system of claim 13 in which the respective first and second sets of cells include one cell each.

15. The system of claim 6 in which the respective first and second sets of cells of at least one of the segments are near each other.

16. The system of claim 6 in which the application's energy range has a minimum wavelength greater than 400 nm and a maximum wavelength less than 1100 nm.

17. The system of claim 6 in which the path includes at least nine segments, the respective subranges of all of the segments being different from each other.

18. The system of claim 6, further comprising:
    a transmission structure that receives photons emanating from the path and, in response, provides photons to the array; the transmission structure providing to the respective second set of cells of each segment photons within the segment's subrange.

19. The system of claim 18 in which the transmission structure further provides photons substantially throughout the application's energy range to the respective first set of cells of each segment.

20. A photon energy sensor that senses photon energies in an application's energy range, the sensor comprising:
- an IC that includes a photosensor array, the array including at least first and second lines of cells, the first and second lines including one or more first-second pairs of cells that are near each other, with a first line cell in each first-second pair being in the first line and a second line cell in each first-second pair being in the second line; and
- over the second line of cells, a second line transmission structure that provides incident photons to cells in the second line;
- for at least one of the first-second pairs of cells, the pair's second line cell receiving from the second line transmission structure incident photons within a respective subrange of the application's energy range and the pair's first line cell receiving incident photons substantially throughout the application's energy range.

21. The sensor of claim 20, further comprising, over the first line of cells, a first line transmission structure that provides incident photons to cells in the first line, the pair's first line cell receiving from the first line transmission structure incident photons substantially throughout the application's energy range.

22. The sensor of claim 21 in which the first line transmission structure is a gray filter.

23. The sensor of claim 20 in which the first and second lines are adjacent straight lines of cells, each first-second pair of cells being a pair of adjacent cells.

24. The sensor of claim 20 in which the pair's first cell is substantially equal to or smaller in sensing area than the pair's second cell.

25. The sensor of claim 20 in which the array further includes a third line of cells, the second and third lines including one or more second-third pairs of cells that are near each other, with a second line cell in each second-third pair being in the second line and a third line cell in each second-third pair being in the third line; the pair's third line cell receiving photons substantially throughout the application's energy range; at least one cell in the second line being the second line cell both of a first-second pair and a second-third pair.

26. The sensor of claim 25 in which the second line cell is between the first line cell in the first-second pair and the third line cell in the second-third pair.

27. The sensor of claim 25 in which the second line cell and the paired first and third line cells all have different sensing areas from each other.

28. The sensor of claim 20 in which the array further includes:
- a third line of cells; and
- over the third line of cells, a third transmission structure that provides incident photons to cells in the third line;
- the first and third lines including one or more first-third pairs of cells that are near each other, with a first line cell in each first-third pair being in the first line and a third line cell in each first-third pair being in the third line; for at least one of the first-third pairs of cells, the pair's third line cell receiving from the third line transmission structure incident photons within a respective subrange of the application's energy range and the pair's first line cell receiving incident photons substantially throughout the application's energy range; at least one cell in the first line being the first line cell both of a first-second pair and a first-third pair.

29. The sensor of claim 28 in which the first line cell is between the second line cell in the first-second pair and the third line cell in the first-third pair.

30. A method of producing a sensor as in claim 20, the method comprising:
- producing the photon energy sensor with the second line transmission structure over at least the second line of cells; for at least one of the first-second pairs of cells, the pair's first cell receiving incident photons substantially throughout an application's energy range and the pair's second cell receiving from the second line transmission structure incident photons within a respective subrange of the application's energy range.

* * * * *